(12) United States Patent
Deveaux et al.

(10) Patent No.: US 8,575,125 B2
(45) Date of Patent: Nov. 5, 2013

(54) SELECTIVE INHIBITORS OF CB2 RECEPTOR EXPRESSION AND/OR ACTIVITY FOR THE TREATMENT OF OBESITY AND OBESITY-RELATED DISORDERS

(75) Inventors: Vanessa Deveaux, Vincennes (FR); Fatima Teixeira Clerc, Rosny Sous Bois (FR); Sylvie Manin, Maisons Alfort (FR); Sophie Lotersztajn, Paris (FR); Ariane Mallat, Paris (FR); Jeanne Tran-Van-Nhieu, Saint Maur des Fosses (FR)

(73) Assignee: Institut National de la Sante et de la Recherche Medicale (INSERM), Paris (FR)

( * ) Notice: Subject to any disclaimer, the term of this patent is extended or adjusted under 35 U.S.C. 154(b) by 0 days.

(21) Appl. No.: 13/297,993

(22) Filed: Nov. 16, 2011

(65) Prior Publication Data

US 2012/0115931 A1    May 10, 2012

Related U.S. Application Data

(62) Division of application No. 12/594,416, filed as application No. PCT/EP2008/054109 on Apr. 4, 2008, now Pat. No. 8,084,422.

(30) Foreign Application Priority Data

Apr. 4, 2007    (EP) .................................... 07290411

(51) Int. Cl.
| | | |
|---|---|---|
| *A61K 48/00* | (2006.01) | |
| *C07H 21/02* | (2006.01) | |
| *C07H 21/04* | (2006.01) | |
| *C12N 15/63* | (2006.01) | |

(52) U.S. Cl.
USPC .......... 514/44; 536/23.1; 536/24.5; 435/320.1

(58) Field of Classification Search
None
See application file for complete search history.

(56) References Cited

U.S. PATENT DOCUMENTS 6,506,559 B1 *    1/2003    Driver et al. ................. 435/6.16

* cited by examiner

*Primary Examiner* — Amy Bowman
(74) *Attorney, Agent, or Firm* — B. Aaron Schulman; Stites & Harbison, PLLC

(57) ABSTRACT

The invention relates to a method for treating and/or preventing obesity and/or obesity-related disorders by administering to a subject in need thereof a selective inhibitor of cannabinoid type 2 (CB2) receptor expression.

4 Claims, 9 Drawing Sheets

SEQUENCE LISTING

```
<160> NUMBER OF SEQ ID NOS: 22

<210> SEQ ID NO 1
<211> LENGTH: 20
<212> TYPE: DNA
<213> ORGANISM: Artificial
<220> FEATURE:
```

<223> OTHER INFORMATION: primer

<400> SEQUENCE: 1
gtaacccgtt gaaccccatt                                         20

<210> SEQ ID NO 2
<211> LENGTH: 20
<212> TYPE: DNA
<213> ORGANISM: Artificial
<220> FEATURE:
<223> OTHER INFORMATION: primer

<400> SEQUENCE: 2
ccatccaatc ggtagtagcg                                         20

<210> SEQ ID NO 3
<211> LENGTH: 20
<212> TYPE: DNA
<213> ORGANISM: Artificial
<220> FEATURE:
<223> OTHER INFORMATION: primer

<400> SEQUENCE: 3
gggcaaattt ccttgtagca                                         20

<210> SEQ ID NO 4
<211> LENGTH: 20
<212> TYPE: DNA
<213> ORGANISM: Artificial
<220> FEATURE:
<223> OTHER INFORMATION: primer

<400> SEQUENCE: 4
tctgcaaggc cgtctaagat                                         20

<210> SEQ ID NO 5
<211> LENGTH: 20
<212> TYPE: DNA
<213> ORGANISM: Artificial
<220> FEATURE:
<223> OTHER INFORMATION: primer

<400> SEQUENCE: 5
ggatacagaa tagccaggac                                         20

<210> SEQ ID NO 6
<211> LENGTH: 20
<212> TYPE: DNA
<213> ORGANISM: Artificial
<220> FEATURE:
<223> OTHER INFORMATION: primer

<400> SEQUENCE: 6
ggagccgttg gtcacttctg                                         20

<210> SEQ ID NO 7
<211> LENGTH: 19
<212> TYPE: DNA
<213> ORGANISM: Artificial
<220> FEATURE:
<223> OTHER INFORMATION: primer

<400> SEQUENCE: 7
gggcctgctg ttcacagtt                                          19

<210> SEQ ID NO 8

```
<211> LENGTH: 19
<212> TYPE: DNA
<213> ORGANISM: Artificial
<220> FEATURE:
<223> OTHER INFORMATION: primer

<400> SEQUENCE: 8
ccagcctact cattgggat                                                      19

<210> SEQ ID NO 9
<211> LENGTH: 22
<212> TYPE: DNA
<213> ORGANISM: Artificial
<220> FEATURE:
<223> OTHER INFORMATION: primer

<400> SEQUENCE: 9
ctttggctat gggcttccag tc                                                  22

<210> SEQ ID NO 10
<211> LENGTH: 24
<212> TYPE: DNA
<213> ORGANISM: Artificial
<220> FEATURE:
<223> OTHER INFORMATION: primer

<400> SEQUENCE: 10
gcaaggagga cagagtttat cgtg                                                24

<210> SEQ ID NO 11
<211> LENGTH: 22
<212> TYPE: DNA
<213> ORGANISM: Artificial
<220> FEATURE:
<223> OTHER INFORMATION: primer

<400> SEQUENCE: 11
aatggcctcc ctctcatcag tt                                                  22

<210> SEQ ID NO 12
<211> LENGTH: 21
<212> TYPE: DNA
<213> ORGANISM: Artificial
<220> FEATURE:
<223> OTHER INFORMATION: primer

<400> SEQUENCE: 12
ccacttggtg gtttgctacg a                                                   21

<210> SEQ ID NO 13
<211> LENGTH: 21
<212> TYPE: DNA
<213> ORGANISM: Artificial
<220> FEATURE:
<223> OTHER INFORMATION: primer

<400> SEQUENCE: 13
gaacaacgat gatgcacttg c                                                   21

<210> SEQ ID NO 14
<211> LENGTH: 21
<212> TYPE: DNA
<213> ORGANISM: Artificial
<220> FEATURE:
<223> OTHER INFORMATION: primer

<400> SEQUENCE: 14
```

```
tccaggtagc tatggtactc c                                              21

<210> SEQ ID NO 15
<211> LENGTH: 23
<212> TYPE: DNA
<213> ORGANISM: Artificial
<220> FEATURE:
<223> OTHER INFORMATION: primer

<400> SEQUENCE: 15
gaagcgctac cggtcttcta tca                                            23

<210> SEQ ID NO 16
<211> LENGTH: 23
<212> TYPE: DNA
<213> ORGANISM: Artificial
<220> FEATURE:
<223> OTHER INFORMATION: primer

<400> SEQUENCE: 16
aagctgacac caggtccttc agt                                            23

<210> SEQ ID NO 17
<211> LENGTH: 21
<212> TYPE: DNA
<213> ORGANISM: Artificial
<220> FEATURE:
<223> OTHER INFORMATION: primer

<400> SEQUENCE: 17
aacctggtga agctggacct a                                              21

<210> SEQ ID NO 18
<211> LENGTH: 20
<212> TYPE: DNA
<213> ORGANISM: Artificial
<220> FEATURE:
<223> OTHER INFORMATION: primer

<400> SEQUENCE: 18
gccacagtga aatctcgttg                                                20

<210> SEQ ID NO 19
<211> LENGTH: 20
<212> TYPE: DNA
<213> ORGANISM: Artificial
<220> FEATURE:
<223> OTHER INFORMATION: primer

<400> SEQUENCE: 19
catctgctgg ccttctccaa                                                20

<210> SEQ ID NO 20
<211> LENGTH: 21
<212> TYPE: DNA
<213> ORGANISM: Artificial
<220> FEATURE:
<223> OTHER INFORMATION: primer

<400> SEQUENCE: 20
atccaggctc tctggcttct g                                              21

<210> SEQ ID NO 21
<211> LENGTH: 22
<212> TYPE: DNA
<213> ORGANISM: Artificial
<220> FEATURE:
```

```
<223> OTHER INFORMATION: primer

<400> SEQUENCE: 21
accagagcga aagcatttgc ca                                             22

<210> SEQ ID NO 22
<211> LENGTH: 22
<212> TYPE: DNA
<213> ORGANISM: Artificial
<220> FEATURE:
<223> OTHER INFORMATION: primer

<400> SEQUENCE: 22
atcgccagtc ggcatcgttt at                                             22
```

SELECTIVE INHIBITORS OF CB2 RECEPTOR EXPRESSION AND/OR ACTIVITY FOR THE TREATMENT OF OBESITY AND OBESITY-RELATED DISORDERS

CROSS-REFERENCE TO RELATED APPLICATIONS

This application is a divisional of U.S. application Ser. No. 12/594,416, filed Oct. 2, 2009 now U.S. Pat. No. 8,084,422, which was a 371 of PCT/EP2008/54109, filed on Apr. 4, 2008, all of said applications incorporated herein by reference.

FIELD OF THE INVENTION

The invention relates to the use of a selective inhibitor of CB2 receptor expression and/or activity for the manufacture of a medicament indented for the treatment and/or the prevention of obesity and obesity-related disorders.

BACKGROUND OF THE INVENTION

Obesity is a condition characterized by an excess of body fat. The prevalence of overweight and obesity is considered an important public health issue in the world. Roughly two thirds of US adults meet the criteria for overweight or obesity. Actually, obesity is an important risk factor for coronary heart disease (CHD), ventricular dysfunction, congestive heart failure, stroke, and cardiac arrhythmias. Furthermore obesity is closely associated with type 2 diabetes, metabolic syndrome and hepatic disorders such as non-alcoholic fatty liver disease.

Type 2 diabetes, or non insulin-dependent diabetes mellitus (NIDDM), is characterized by the fact that patient produce insulin and even exhibit hyperinsulinemia (plasma insulin levels that are the same or even elevated in comparison with non-diabetic subjects), while at the same time demonstrating hyperglycemia. Type 2 diabetics often develop "insulin resistance", such that the effect of insulin in stimulating glucose and lipid metabolism in the main insulin-sensitive tissues, namely, muscle, liver and adipose tissues, is diminished and those patients are thus at increased risk of cardiovascular complications, e.g. atherosclerosis, coronary heart disease, stroke, peripheral vascular disease, hypertension, nephropathy, neuropathy and retinopathy.

Many patients who have insulin resistance, but have not developed type 2 diabetes, are also at a risk of developing symptoms referred to as Metabolic Syndrome. Metabolic syndrome is characterized by insulin resistance, along with abdominal obesity, hyperinsulinemia, high blood pressure, low HDL and high VLDL. These patients, whether or not they develop overt diabetes mellitus, are at increased risk of developing cardiovascular complications.

Furthermore epidemiologic evidences suggest that obesity increases the risk of cirrhosis. For example, in autopsy series, obesity was identified as the only risk factor for disease in 12% of cirrhotic subjects (Yang, S. Q. et al.; 1997). Notably, cirrhosis is approximately six times more prevalent in obese individuals than in the general population. The degree of obesity correlates positively with the prevalence and severity of fatty liver (steatosis), and this in turn correlates with steatohepatitis.

Thus, there is a need for treating obesity and obesity-related disorders, such as NIDDM, metabolic syndrome or non-alcoholic fatty liver disease.

Weight loss drugs that are currently used for the treatment of obesity have limited efficacy and significant side effects. Studies of the weight loss medications orlistat (Davidson M H. et al. 1999), dexfenfluramine (Guy-Grand, B. et al. 1989), sibutramine (Bray, G. A. et al. 1999) and phentermine (Douglas, A. et al. 1983) have demonstrated a limited weight loss of about 5%-10% of body weight for drug compared to placebo. However the side effects of these drugs limit their use. For instance dexfenfluramine was withdrawn from the market because of suspected heart valvulopathy; orlistat is limited by gastrointestinal side effects; the use of topiramate is limited by central nervous system effects; and the use of sibutramine is limited by its cardiovascular side effects which have led to reports of deaths and its withdrawal from the market in Italy.

Recent studies suggest that antagonists of the cannabinoid receptor type 1 (CB1) may be useful for the treatment of obesity and obesity-related disorders. For example, the international patent publication WO2005/046689 discloses CB1 antagonists derived from pyrazole for the treatment or prevention of obesity and obesity related disorders. More specifically, Rimonabant (SR 141716), which is a selective cannabinoid CB1 receptor antagonist, has undergone extensive testing in the treatment of obesity. In 4 clinical studies with more than 6000 overweight and obese patients (Rimonabant in Obesity (RIO) program), rimonabant has demonstrated consistent efficacy with regard to weight loss and reduction of the associated cardiometabolic risks (Van Gaal L F. et al. 2005; Després J P. et al. 2005; Pi-Sunyer F X. et al. 2006).

On the contrary, the only studies available on that subject, performed with antagonists of the cannabinoid receptor type 2 (CB2) ruled out that they may show beneficial effect on obesity and obesity-related disorders based on their absence of effect on food intake or locomotor activity (Wiley J L et al. 2005; Williams C M. et al. 2002).

The international patent application WO 98/31227 previously described pyrazole derivatives which are said to be modulators (antagonist or agonist) of CB2 receptor. The disclosed modulators were suggested to be useful for the treatment of immunologically mediated inflammatory diseases, including diabetes. However, it was not specified whether an antagonist or agonist of CB2 receptor should be used for that treatment and the proposed application was purely speculative.

The international patent application WO 2006/105217 further suggested that CB2 receptor inhibitors are expected to have therapeutical utility in the control of diabetes, cerebral stroke and cerebral ischemia. However, these therapeutical applications were also purely speculative.

The instant application formally demonstrates that CB2 receptor plays a major role in the development of obesity, insulin resistance, inflammation and hepatic steatosis. Hence, a new pathway for the treatment and/or the prevention of obesity and obesity-related disorders is provided which involves interfering with CB2 receptor expression and/or activity.

SUMMARY OF THE INVENTION

The invention relates to the use of a selective inhibitor of CB2 receptor expression and/or activity for the manufacture of a medicament intended for the treatment and/or the prevention of obesity and obesity-related disorders.

In one aspect, the invention makes use of a selective inhibitor of CB2 receptor expression.

According to preferred embodiments, said inhibitor of CB2 receptor expression is selected from the group consisting of antisense RNA or DNA molecules, small inhibitory RNAs (SiRNAs) and ribozymes.

In another aspect of the invention, the inhibitor selectively antagonizes CB2 receptor activity ("CB2 receptor antagonist").

According to preferred embodiments, said CB2 receptor antagonist is selected from the group consisting of small organic molecules, partial or complete CB2 receptor blocking antibodies or antibody fragments and aptamers.

BRIEF DESCRIPTION OF THE DRAWING FIGURES

FIG. 1: Body weight of WT and CB2-/- mice fed a high fat diet. Wild type mice (n=22) and CB2-/- mice (n=10) were fed either standard chow or high fat diet (HFD). Body weight was measured weekly.

FIG. 2: Average food intake of WT and CB2-/- mice over 15 weeks of high fat diet (HFD).

FIG. 3: Adipocyte size was quantified on at least 30 cells from 3 separate fields in 7 WT and 5 CB2-/- high fat diet fed animals, using Image J software.*p<0.05 for WT vs CB2-/- HFD mice.

FIG. 4: Fasting blood glucose concentrations in WT (n=7) and CB2-/- mice (n=5) fed a high fat diet. p=0.07 for WT vs CB2-/- HFD mice.

FIG. 5: Fasting serum insulin concentrations in WT (n=7) and CB2-/- mice (n=5) fed a high fat diet. p=0.06 for WT vs CB2-/- HFD mice.

FIG. 6: Serum leptin levels in WT (n=7) and CB2-/- mice (n=5) fed a high fat diet. *p<0.05 for WT vs CB2-/- HFD mice.

Figure 10:
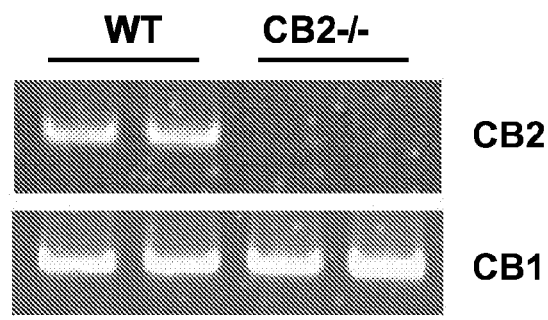

FIG. 10: Differential regulation of CB1 and CB2 receptor mRNA expression in adipose tissue and liver of WT (n=7) and CB2-/- (n=5) mice under control and HFD for 15 weeks. CB2-/- mice do not express the CB2 gene, but display normal CB1 gene expression. A band of by corresponding to the expected size of the CB2 receptor PCR product was identified in liver of WT mice, but not in the liver of CB2-/- mice. A band of by corresponding to the expected size of the CB1 receptor PCR product was identified in liver of WT and CB2-/- mice.

Figure 11:
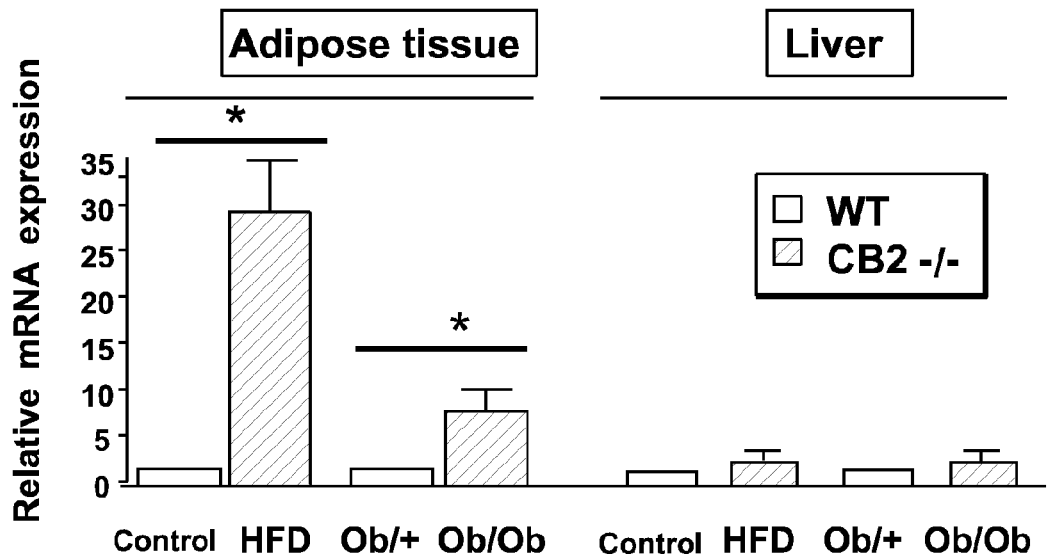

FIG. 11 shows CB2 receptor mRNA expression in adipose tissue and liver. *p<0.05 for WT vs CB2-/- HFD mice p<0.05 vs mice under control diet.

Figure 12:
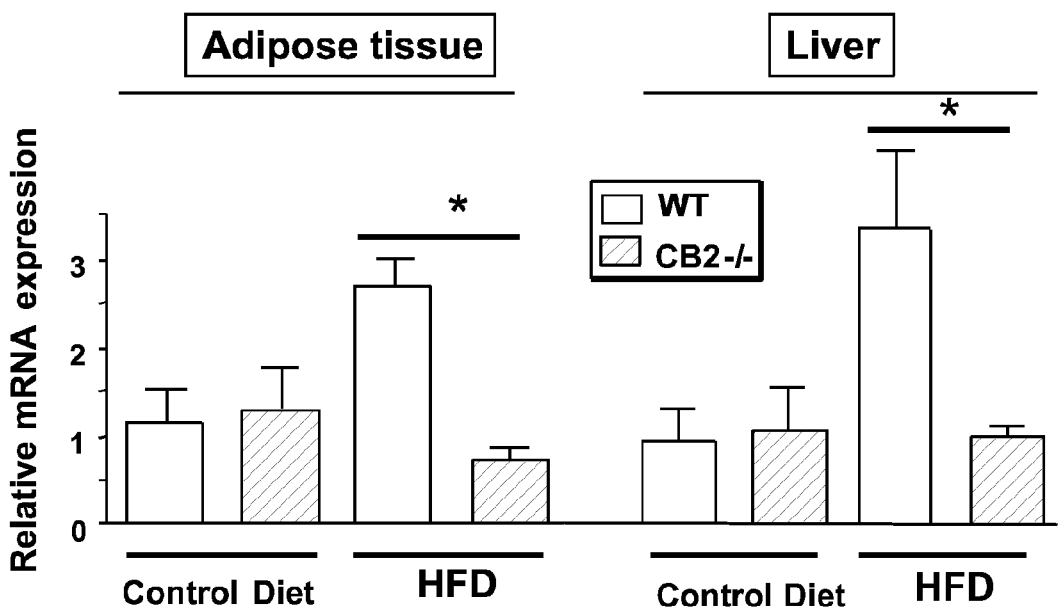

FIG. 12 shows CB1 receptor mRNA expression in adipose tissue and liver. *p<0.05 for WT vs CB2-/- HFD mice. P<0.05 vs mice under control diet.

Figure 13:
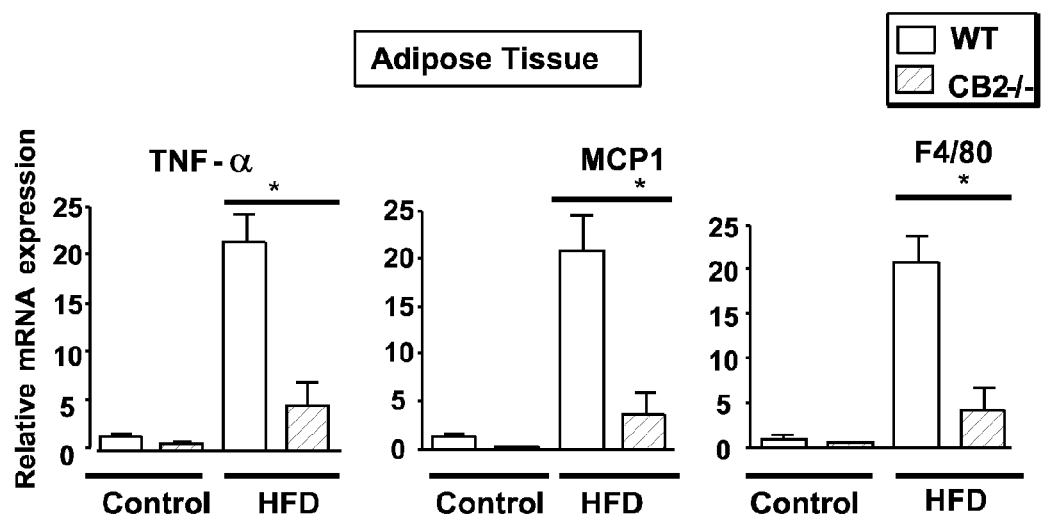

FIG. 13 shows reduced inflammation in epididymal adipose tissue (EAT) of HFD-fed CB2-/- mice. F4/80, TNF-alpha, and MCP-1 mRNA expressions in WT and CB2-/- mice fed with HFD or control diet. *p<0.05 for WT vs CB2-/- HFD mice. P<0.05 vs mice under control diet.

Figure 14:
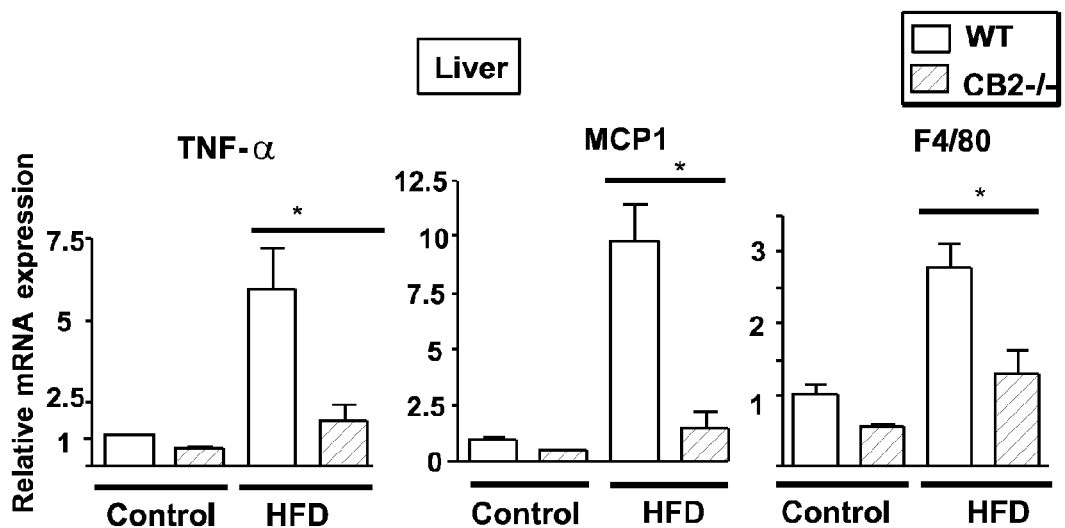

FIG. 14 shows reduced inflammation in liver of HFD-fed CB2-/- mice. F4/80, TNF-alpha, and MCP-1 mRNA expressions in WT and CB2-/- mice fed with HFD or control diet. *p<0.05 for WT vs CB2-/- HFD mice. P<0.05 vs mice under control diet.

Figure 15:
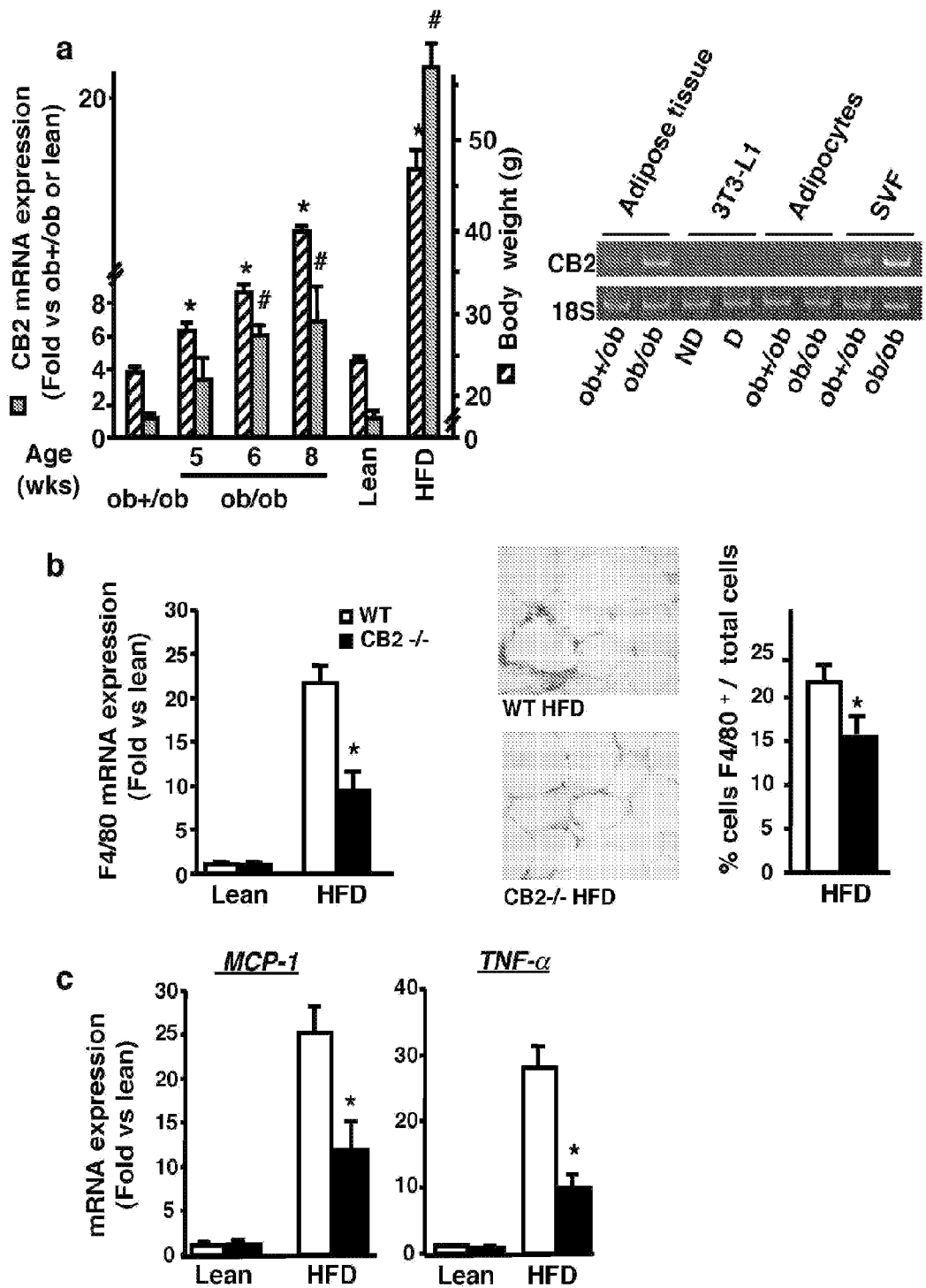

FIG. 15a shows on the left panel quantification of CB2 receptor mRNA in the epididymal adipose tissue and corresponding body weight in lean ob+/ob (n=5) and obese ob/ob mice aged 5, 6 or 8 weeks (n=5/group). Body weight was measured in parallel. (*, #, p<0.05 for ob/ob vs ob/+ mice) in obese HFD-fed wild mice and their lean counterparts. *p<0.05 vs mice under control diet.

FIG. 15a shows on the right panel CB2 receptor mRNA expression in the stromal vascular fraction (SVF) of adipose tissue and in the adipocyte fraction. CB2 receptor mRNA is expressed in SVF of adipose tissue and undetectable in the adipocyte fraction. CB2 mRNA was quantified in the SVF and adipocyte fractions of ob/ob and ob+/ob mice, and in the non differenciated (ND) and differenciated (D) 3T3-L1 adipocyte cell line.

FIG. 15b shows on the left panel the quantification of macrophage-related (F4/80) mRNA expression in epididymal fat of WT and CB2-/- mice fed a HFD or control diet.

FIG. 15b shows on the middle panel macrophage infiltration into epididymal fat by immunohistochemical detection of F4/80 (magnification ×400).

FIG. 15b shows on the right panel quantification of F4/80 stained cells/total cells on the basis of immunhistochemical detection of F4/80.

FIG. 15c shows MCP-1 and TNF-alpha mRNA expression in the epididymal fat of WT and CB2-/- mice fed a HFD vs lean mice.

Figure 16:
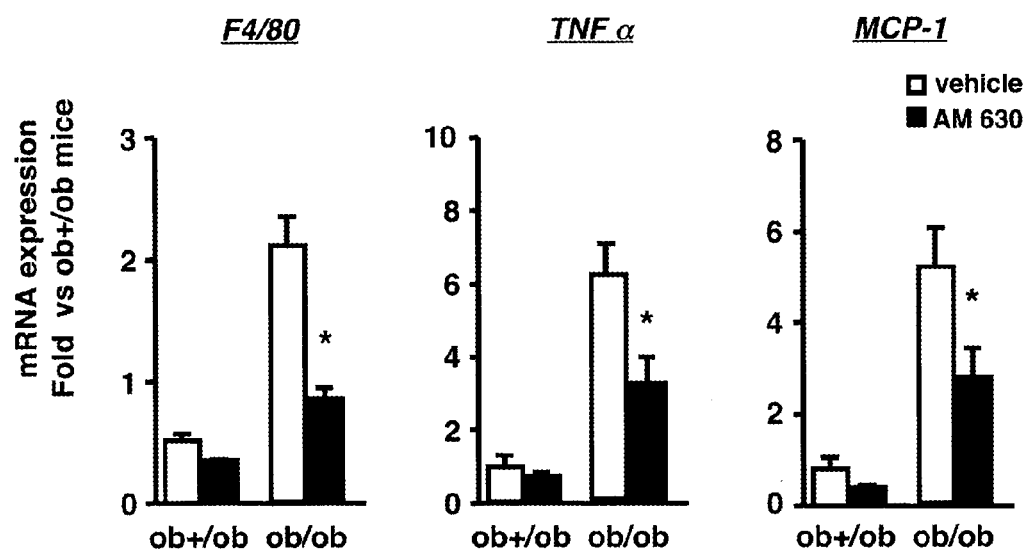

FIG. 16 shows the impact of the CB2 antagonist AM 630 on epididymal fat inflammatory gene expression, following a 17 day-treatment. Macrophage-related F4/80, TNF-alpha and MCP-1 mRNA expressions were quantified in the epididymal fat in vehicle and AM630-treated ob/ob mice. *p<0.05 for vehicle vs AM630 or SR 144528 ob/ob mice.

DETAILED DESCRIPTION OF THE INVENTION

Definitions

A "coding sequence" or a sequence "encoding" an expression product, such as an RNA, polypeptide, protein, or enzyme, is a nucleotide sequence that, when expressed, results in the production of that RNA, polypeptide, protein, or enzyme, i.e., the nucleotide sequence encodes an amino acid sequence for that polypeptide, protein or enzyme. A coding sequence for a protein may include a start codon (usually ATG) and a stop codon.

As used herein, references to specific proteins (e.g., CB2 receptor) can include a polypeptide having a native amino acid sequence, as well as variants and modified forms regardless of their origin or mode of preparation. A protein that has a native amino acid sequence is a protein having the same amino acid sequence as obtained from nature (e.g., CB2 receptor). Such native sequence proteins can be isolated from nature or can be prepared using standard recombinant and/or synthetic methods. Native sequence proteins specifically encompass naturally occurring truncated or soluble forms, naturally occurring variant forms (e.g., alternatively spliced forms), naturally occurring allelic variants and forms including post-translational modifications. A native sequence protein includes proteins following post-translational modifications such as glycosylation, or phosphorylation, or other modifications of some amino acid residues.

Variants refer to proteins that are functional equivalents to a native sequence protein that have similar amino acid sequences and retain, to some extent, one or more activities of the native protein. Variants also include fragments that retain activity. Variants also include proteins that are substantially identical (e.g., that have 80, 85, 90, 95, 97, 98, 99%, sequence identity) to a native sequence. Such variants include proteins having amino acid alterations such as deletions, insertions and/or substitutions. A "deletion" refers to the absence of one or more amino acid residues in the related protein. The term "insertion" refers to the addition of one or more amino acids in the related protein. A "substitution" refers to the replacement of one or more amino acid residues by another amino acid residue in the polypeptide. Typically, such alterations are conservative in nature such that the activity of the variant protein is substantially similar to a native sequence protein (see, e.g., Creighton (1984) Proteins, W.H. Freeman and Company). In the case of substitutions, the amino acid replacing another amino acid usually has similar structural and/or chemical properties. Insertions and deletions are typically in the range of 1 to 5 amino acids, although depending upon the location of the insertion, more amino acids can be inserted or removed. The variations can be made using methods known in the art such as site-directed mutagenesis (Carter, et al. 1985; Nucl. Acids Res. 13:4331; Zoller et al. 1982), cassette mutagenesis (Wells et al. 1985), and PCR mutagenesis (Sambrook et al., Molecular Cloning: A Laboratory Manual, 3rd edition, Cold Spring Harbor Press, N.Y., (2001)).

Two amino acid sequences are "substantially homologous" or "substantially similar" when greater than 80%, preferably greater than 85%, still preferably greater than 90% of the amino acids are identical, or greater than about 90%, preferably greater than 95%, are similar (functionally identical) over the whole length sequences. Preferably, the similar or homologous sequences are identified by alignment using, for example, the GCG (Genetics Computer Group, Program Manual for the GCG Package, Version 7, Madison, Wis.) pileup program, or any of sequence comparison algorithms such as BLAST, FASTA, etc.

A "receptor" or "receptor molecule" is a soluble or membrane bound/associated protein or glycoprotein comprising one or more domains to which a ligand binds to form a receptor-ligand complex. By binding the ligand, which may be an agonist or an antagonist, the receptor is activated or inactivated and may initiate or block pathway signalling.

As used herein, the term "selective inhibitor of CB2 receptor expression and/or activity" denotes a natural or synthetic compound which acts as a selective inhibitor of CB2 receptor expression and/or as a selective inhibitor of CB2 receptor activity, i.e. as a CB2 receptor antagonist.

The term "CB2 receptor" has its general meaning in the art (Pertwee, R. G. 1999) and refers to the cannabinoid receptor type 2. The term may include naturally occurring CB2 receptors and variants and modified forms thereof. The term may also refer to fusion proteins in which a domain from CB2 that retains at least one CB2 activity is fused, for example, to another polypeptide (e.g., a polypeptide tag such as His tag is conventional in the art). The CB2 receptor can be from any source, but typically is a mammalian (e.g., human and non-human primate) CB2, particularly a human CB2. An exemplary native CB2 amino acid sequence is provided in GenPept database under accession number NP_001832 and an exemplary native CB2 nucleotide sequence is provided in GenBank database under accession number NM_001841.

The term "expression" when used in the context of expression of a gene or nucleic acid refers to the conversion of the information, contained in a gene, into a gene product. A gene product can be the direct transcriptional product of a gene (e.g., mRNA, tRNA, rRNA, antisense RNA, ribozyme, structural RNA or any other type of RNA) or a protein produced by translation of a mRNA. Gene products also include messenger RNAs which are modified, by processes such as capping, polyadenylation, methylation, and editing, and proteins (e.g., CB2 receptor) modified by, for example, methylation, acetylation, phosphorylation, ubiquitination, SUMOylation, ADP-ribosylation, myristilation, and glycosylation.

An "inhibitor of expression" refers to a natural or synthetic compound that has a biological effect to inhibit or significantly reduce the expression of a gene. Consequently an "inhibitor of CB2 receptor expression" refers to a natural or synthetic compound that has a biological effect to inhibit or significantly reduce the expression of the gene encoding for the CB2 receptor gene.

By "ligand" or "receptor ligand" is meant a natural or synthetic compound which binds a receptor molecule to form a receptor-ligand complex. The term ligand includes agonists, antagonists, and compounds with partial agonist/antagonist action.

A "receptor agonist" is a natural or synthetic compound which binds the receptor to form a receptor-agonist complex by activating said receptor and receptor-agonist complex, respectively, initiating a pathway signalling and further biological processes. Examples of selective CB2 receptor agonists include JWH133 or AM1241. Reference may be made also to DELTA-9-THC, WIN55212-2 and CP55,940 which are mixt CB1/CB2 receptor agonists.

By "receptor antagonist" is meant a natural or synthetic compound that has a biological effect opposite to that of a receptor agonist. The term is used indifferently to denote a "true" antagonist and an inverse agonist of a receptor. A "true" receptor antagonist is a compound which binds the receptor and blocks the biological activation of the receptor, and thereby the action of the receptor agonist, for example, by competing with the agonist for said receptor. An inverse agonist is a compound which binds to the same receptor as the agonist but exerts the opposite effect. Inverse agonists have the ability to decrease the constitutive level of receptor activation in the absence of an agonist.

The term "CB2 receptor antagonist" refers to any CB2 receptor antagonist (true antagonist or inverse agonist) that is currently known in the art or that will be identified in the future, and includes any chemical entity that, upon administration to a patient, results in inhibition or down-regulation of a biological activity associated with activation of the CB2 receptor in the patient, including any of the downstream biological effects otherwise resulting from the binding to CB2 receptor of its natural ligand. Such CB2 receptor antagonists include any agent that can block CB2 receptor activation or any of the downstream biological effects of CB2 receptor activation. For example, such a CB2 receptor antagonist can act by occupying the ligand binding site or a portion thereof of the CB2 receptor, thereby making the receptor inaccessible to its natural ligand so that its normal biological activity is prevented or reduced.

In the context of the present invention, CB2 receptor antagonists are selective for the CB2 receptor as compared with the CB1 receptor. By "selective" it is meant that the affinity of the antagonist for the CB2 receptor is at least 10-fold, preferably 25-fold, more preferably 100-fold, still preferably 300-fold higher than the affinity for the CB1 receptor.

The affinity of an antagonist for CB1 (or CB2) receptor may be quantified by measuring the activity of CB1 (or CB2) receptor in the presence of a range of concentrations of said antagonist in order to establish a dose-response curve. From that dose response curve, an $IC_{50}$ value may be deduced which represents the concentration of antagonist necessary to inhibit 50% of the response to an agonist in defined concentration, for instance CP 55,940 at 3 nM or below. The $IC_{50}$ value may be readily determined by the one skilled in the art by fitting the dose-response plots with a dose-response equation as described by De Lean et al. (1979). $IC_{50}$ values can be converted into affinity constant (Ki) using the assumptions of Cheng and Prusoff (1973).

Accordingly, a CB2 receptor antagonist is a compound for which at least one of the ratios (i) $K_i$ CB1: $K_i$ CB2, and (ii) $IC_{50}$ CB1: $IC_{50}$ CB2, is above 10:1, preferably 25:1, more preferably 100:1, still preferably 300:1, as may be measured using one of the following assays.

The antagonistic activity of compounds towards the CB1 and CB2 receptors may be determined using various methods. For example, it is known that CB1/CB2 receptor agonists (DELTA-9-THC, WIN 55212-2 or CP 55,940) are capable of inhibiting the adenylate cyclase activity induced by Forskolin. Thus, the affinity of an antagonist for CB1 and CB2 receptor may be assayed by determining the ability of said antagonist to block the effect of the CB1/CB2 receptor agonists in a cAMP measurement assay.

In particular, a cAMP accumulation measurement assay has been described in Rinaldi-Carmona et al. (1998) in view of Matsuda et al. (1990) and Rinaldi-Carmona et al. (1996). Briefly, CHO cells stably transformed with CB1 or CB2 are grown to confluence, washed with PBS and incubated for 15 min at 37° C. in 1 ml of PBS (containing 0.25% acid-free BSA, 0.1 mM IBMX, 0.2 mM RO20-1724) in the absence or in the presence of 3 nM CP 55,940, or the antagonist to be assayed (for instance $10^{-9}$-$10^{-6}$M), or 3 nM CP 55,940 plus the antagonist to be assayed (for instance $10^{-9}$-$10^{-5}$M). Forskolin (3 µM final concentration) is added and cells are incubated for another 20 min at 37° C. The reaction is terminated by rapid aspiration of the assay medium and addition of 1.5 ml of ice-cold 50 mM Tris-HCl, pH 8, 4 mM ethylenediaminetetraacetic acid. Dishes are placed on ice for 5 min and then the extracts are transferred to a glass tube. Extracts are boiled and centrifuged for 10 min at 3500 g to eliminate cell debris. Aliquots from supernatant are dried and the cAMP concentration is determined according to any suitable method. The one skilled in the art may in particular make use of one of the many commercial kits available for cAMP measurement. The basal activity is determined in the absence of forskolin.

Alternatively, binding assays may be used. In particular binding assays with tritiated CB1/CB2 agonist may be carried out on membranes prepared from rat forebrain membranes (CB1) or membranes prepared from frozen mouse spleen (CB2). Reference may be made for instance to the assay described in the U.S. patent specification US2006030563.

Briefly, the membranes for the CB1 and CB2 receptors binding studies may be prepared as described in Dodd et al. (1981). The CB1 and CB2 binding assays are conducted in the same manner, according to the following protocol method adapted from Devane et al. (1988) and Charalambous et al. (1992) with the following changes. Membranes, frozen at −80° C., are thawed on ice. Three volumes of TME (25 mM Tris-HCl buffer, 5 mM $MgCl_2$ and 1 mM EDTA) at pH 7.4 are added. The suspension is incubated at 4° C. for 30 min. At the end of the incubation, the membranes are pelleted and washed three times with TME.

The treated membranes are subsequently used in the binding assay: approximately 30 µg of membranes are incubated in silanized 96-well microtiter plate with TME containing 0.1% essentially fatty acid-free bovine serum albumin (BSA), 0.8 nM [$^3$H] CP-55,940, and various concentrations of antagonist at 30° C. for 1 hour. The samples are filtered, for instance using Packard Filtermate 196 and Whatman GF/C filterplates, and washed with wash buffer (TME containing 0.5% BSA). Radioactivity is detected according to any suitable method. Non specific binding is assessed using 100 nM CP-55,940. Data collected are normalized between 100% and 0% specific binding for [$^3$H] CP-55,940, determined using buffer and 100 nM CP-55,940. The normalized data are analyzed using a 4-parameter nonlinear logistic equation to yield $IC_{50}$ values which are converted to $K_i$ values using the assumptions of Cheng et Prusoff (1973). The term "small organic molecule" refers to a molecule of a size comparable to those organic molecules generally used in pharmaceuticals. The term excludes biological macromolecules (e.g., proteins, nucleic acids, etc.). Preferred small organic molecules range in size up to about 5000 Da, more preferably up to 2000 Da, and most preferably up to about 1000 Da.

By "purified" and "isolated" it is meant, when referring to a polypeptide or a nucleotide sequence, that the indicated molecule is present in the substantial absence of other biological macromolecules of the same type. The term "purified" as used herein preferably means that at least 75% by weight, more preferably at least 85% by weight, still preferably at least 95% by weight, and most preferably at least 98% by weight, of biological macromolecules of the same type are present. An "isolated" nucleic acid molecule which encodes a particular polypeptide refers to a nucleic acid molecule which is substantially free of other nucleic acid molecules that do not encode the subject polypeptide; however, the molecule may include some additional bases or moieties which do not deleteriously affect the basic characteristics of the composition.

As used herein, the term "subject" denotes a mammal, such as a rodent, a feline, a canine, and a primate. Preferably, a subject according to the invention is a human.

The term "obesity" refers to a condition characterized by an excess of body fat. The operational definition of obesity is based on the Body Mass Index (BMI), which is calculated as body weight per height in meter squared ($kg/m^2$). Obesity refers to a condition whereby an otherwise healthy subject has a BMI greater than or equal to 30 $kg/m^2$, or a condition whereby a subject with at least one co-morbidity has a BMI greater than or equal to 27 $kg/m^2$. An "obese subject" is an otherwise healthy subject with a BMI greater than or equal to 30 $kg/m^2$ or a subject with at least one co-morbidity with a BMI greater than or equal 27 $kg/m^2$. A "subject at risk of obesity" is an otherwise healthy subject with a BMI of 25 $kg/m^2$ to less than 30 $kg/m^2$ or a subject with at least one co-morbidity with a BMI of 25 $kg/m^2$ to less than 27 $kg/m^2$. The increased risks associated with obesity may occur at a lower BMI in people of Asian descent. In Asian and Asian-Pacific countries, including Japan, "obesity" refers to a condition whereby a subject with at least one obesity-induced or obesity-related co-morbidity that requires weight reduction or that would be improved by weight reduction, has a BMI greater than or equal to 25 $kg/m^2$. An "obese subject" in these countries refers to a subject with at least one obesity-induced or obesity-related co-morbidity that requires weight reduction or that would be improved by weight reduction, with a BMI greater than or equal to 25 $kg/m^2$. In these countries, a "subject at risk of obesity" is a person with a BMI of greater than 23 $kg/m^2$ to less than 25 $kg/m^2$.

The term "obesity-related disorders" encompasses disorders that are associated with, caused by, or result from obesity. Examples of obesity-related disorders include overeating and bulimia, diabetes, hypertension, elevated plasma insulin concentrations and insulin resistance, dyslipidemia, hyperlipidemia, breast, prostate, endometrial and colon cancer, heart disease, cardiovascular disorders, abnormal heart rhythms and arrhythmias, myocardial infarction, congestive heart failure, coronary heart disease, angina pectoris, cerebral infarction, cerebral thrombosis and transient ischemic attack. Other examples include pathological conditions showing reduced metabolic activity or a decrease in resting energy expenditure as a percentage of total fat-free mass. Further examples of obesity-related disorders include metabolic syndrome, also known as syndrome X, insulin resistance syndrome, type II diabetes, impaired fasting glucose, impaired glucose tolerance, inflammation, such as systemic inflammation of the vasculature, atherosclerosis, hypercholesterolemia, hyperuricaemia, as well as secondary outcomes of obesity such as left ventricular hypertrophy. Obesity-related disorders also include the liver abnormalities associated with obesity such as steatosis or non-alcoholic fatty liver disease (NAFLD) a rising cause of cirrhosis associated to obesity and metabolic syndrome. Indeed, NAFLD can present as simple steatosis or evolve towards inflammation and steatohepatitis (NASH), with a 20% risk of cirrhosis after 20 years. "Dyslipidemia" is a major risk factor for coronary heart disease (CHD). Low plasma levels of high density lipoprotein (HDL) cholesterol with either normal or elevated levels of low density (LDL) cholesterol is a significant risk factor for developing atherosclerosis and associated coronary artery disease in humans. Dyslipidemia is often associated with obesity.

The term "Metabolic Syndrome", or syndrome X, as used herein, is present if a person has three or more of the following symptoms: abdominal obesity, hyperglyceridemia, low HDL cholesterol, high blood pressure, and high fasting plasma glucose. The criteria for these symptoms are defined in the third Report of the National Cholesterol Education Program Expert Panel in Detection, Evaluation and Treatment of High blood Cholesterol in Adults (Ford, E S. et al. 2002).

The term "type II diabetes" or "non-insulin dependent diabetes mellitus (NIDDM)" has its general meaning in the art. Type II diabetes often occurs when levels of insulin are normal or even elevated and appears to result from the inability of tissues to respond appropriately to insulin. Most of the Type II diabetics are obese.

The term "NAFLD" refers to nonalcoholic fatty liver disease. The NAFLD is a disorder with histologic features of alcohol-induced liver disease that occurs in people who do not consume significant amounts of alcohol. NAFLD can present as simple steatosis (defined as fat accumulation into the liver) or evolve towards inflammation and steatohepatitis (NASH), with a 20% risk of cirrhosis after 20 years. The term "NASH" refers to the non-alcoholic steatohepatitis (NASH). NASH is a progressive disease of the liver of unknown etiology characterized histologically by hepatocyte damage and inflammation resembling alcoholic hepatitis. NASH is a critical stage in the process because of the risk of progression to fibrosis, cirrhosis and hepatic failure. Hyperglycemia with and without evidence of hyperlipidemia, obesity and type-2 diabetes are commonly associated with NAFLD and are a predisposing condition. More recent reports have suggested that NAFLD may be more common than originally suspected and that it may affect individuals who lack the typical risk factors for this disorder. Since the prevalence of obesity and type 2 diabetes is increasing, the prevalence of NAFLD is also expected to increase and therefore, this disease has become an emerging public issue (Reid A E. 2001).

Preferred obesity-related disorders may be in particular selected from the group consisting of dyslipidemia, non-insulin-dependent diabetes mellitus, insulin resistance, metabolic syndrome, coronary heart disease, atherosclerosis and non-alcoholic fatty liver disease.

Preferably, obesity and obesity-related diseases are not of genetic origin. In particular, obesity and obesity-related diseases induced by overeating, high fat diet, and/or hyperglycaemic diet are preferably contemplated.

In its broadest meaning, the term "treating" or "treatment" refers to reversing, alleviating, inhibiting the progress of, or preventing the disorder or condition to which such term applies, or one or more symptoms of such disorder or condition.

In particular, "treatment" of obesity and obesity-related disorders may refer to the administration of the compounds or combinations of the present invention to reduce or maintain the body weight of an obese subject. One outcome of treatment may be reducing the body weight of an obese subject relative to that subject's body weight immediately before the administration of the compounds of the present invention. Another outcome of treatment may be preventing body weight regain of body weight previously lost as a result of diet, exercise, or pharmacotherapy. Another outcome of treatment may be decreasing the occurrence of and/or the severity of obesity-related diseases. Another outcome of treatment may be to maintain weight loss.

In particular, "prevention" of obesity and obesity-related disorders may refer to the administration of the compounds of the present invention to reduce or maintain the body weight of a subject at risk of obesity. One outcome of prevention may be reducing the body weight of a subject at risk of obesity relative to that subject's body weight immediately before the administration of the compounds of the present invention. Another outcome of prevention may be preventing body weight regain of body weight previously lost as a result of diet, exercise, or pharmacotherapy. Another outcome of prevention may be preventing obesity from occurring if the treatment is administered prior to the onset of obesity in a subject at risk of obesity. Another outcome of prevention may be decreasing the occurrence and/or severity of obesity-related disorders if the treatment is administered prior to the onset of obesity in a subject at risk of obesity. Another outcome of prevention may be to prolong resistance to weight gain. Another outcome of prevention may be to prevent weight regain. Moreover, if treatment is commenced in already obese subjects, such treatment may prevent the occurrence, progression or severity of obesity-related disorders.

"Pharmaceutically" or "pharmaceutically acceptable" refers to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type.

Therapeutic Methods and Uses

The present invention provides methods and compositions (such as pharmaceutical compositions) for treating obesity and/or obesity-related disorders.

Thus, an object of the invention is the use of a selective inhibitor of CB2 receptor expression and/or activity for the manufacture of a medicament intended for treating obesity and/or obesity-related disorders.

According to a first aspect, the invention relates to the use of a selective inhibitor of CB2 receptor activity (hereafter called "CB2 receptor antagonist").

In one embodiment, the CB2 receptor antagonist may be a low molecular weight antagonist, e.g. a small organic molecule.

Small organic CB2 receptor antagonists that may be used by the invention include, but are not limited to those reviewed in Barth F et al. (1999).

A specific example of small organic CB2 receptor antagonist that can be used according to the present invention is AM630 which was described by Hosohata Y et al. (1997) and has the structure of formula (I):

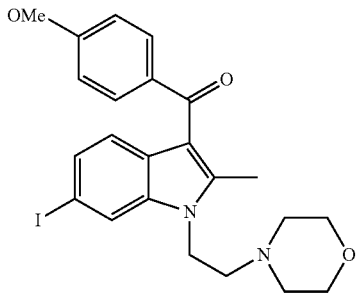 [SMILES: COc1ccc(C(=O)c2c(C)n(CCN3CCOCC3)c3cc(I)ccc23)cc1]

Another specific example of small organic CB2 receptor antagonist which can be used according to the present invention is JTE-907 which was described by Iwamura et al. (2001) and has the structure of formula (II):

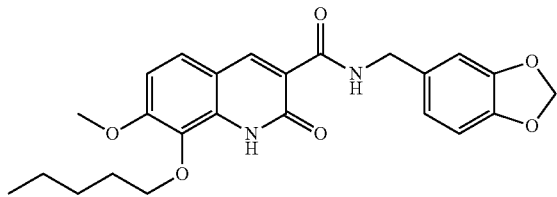 [SMILES: CCCCCOc1c(OC)ccc2cc(C(=O)NCc3ccc4c(c3)OCO4)c(=O)[nH]c12]

A further compound having a pyrazole structure with affinity and selectivity towards CB2 receptors is the compound known with the abbreviation SR144528 (M. Rinaldi-Carmona et al., 1998), the structure of which is reported hereinafter (III):

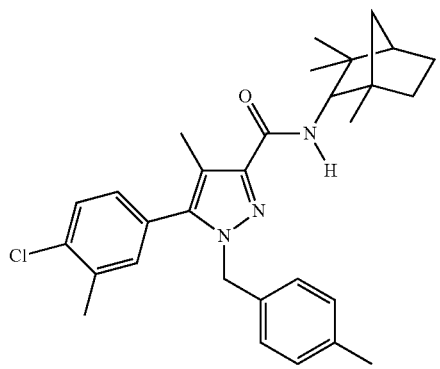 [SMILES: Cc1ccc(Cn2nc(C(=O)NC3C4(C)CCC(C4)C3(C)C)c(C)c2-c2ccc(Cl)c(C)c2)cc1]

The international patent publication WO01/32629 also describes CB2 receptor antagonists, their preparation, and pharmaceutical compositions containing them. Those compounds are included herein by reference. These compounds which may be used in the context of the present invention are tricyclic derivatives of 1-benzylpyrazole-3-carboxylic acid and have the structure of the general formula (IV):

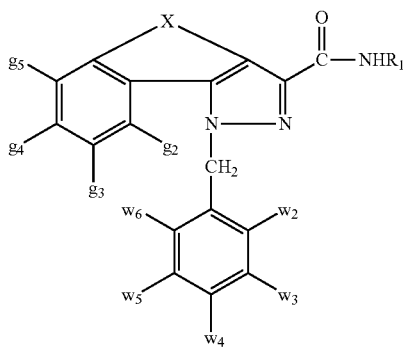

in which:

X— represents a group —$(CH_2)_n$—;

n is equal to 1 or 2;

$g_2$, $g_3$, $g_4$, $g_5$, $w_2$, $w_3$, $w_4$, $w_5$, $w_6$ are identical or different and each independently represent hydrogen, a halogen atom, a trifluoromethyl, a (C1-C4)alkyl, a (C1-C4)alkoxy, a (C1-C4)alkylthio, a nitro; and $R_1$ represents a non aromatic C3-C15 carbocyclic radical which is unsubstituted or substituted one or several times with a (C1-C4)alkyl, or a pharmaceutically acceptable salt or solvate thereof.

Other specific examples of CB2 receptor antagonists include those described in the international patent publication WO 97/21682, and which are included herein by reference. These have the formula (V):

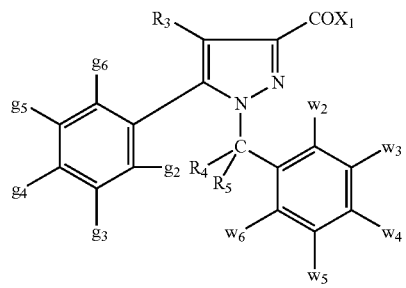

in which:

$X_1$ is a group —$NR_1$, $R_2$ or a group —$OR_2$;

$g_2$, $g_3$, $g_4$, $g_5$, $g_6$ and $w_2$, $w_3$, $w_4$, $w_5$, $w_6$ are identical or different and are each independently hydrogen, a halogen atom, a (C1-C4)alkyl, a (C1-C4)alkoxy, a trifluoromethyl, a nitro or a (C1-C4)alkylthio, with the proviso that at least one of the substituents $g_2$, $g_3$, $g_4$, $g_5$, $g_6$ and at least one of the substituents $w_2$, $w_3$, $w_4$, $w_5$, $w_6$ are other than hydrogen;

$R_1$ is hydrogen or a (C1-C4)alkyl;

$R_2$ is a non-aromatic (C3-C15)carbocyclic radical which is unsubstituted or monosubstituted or polysubstituted by a substituent selected from a halogen atom, a (C1-C4)alkyl and a (C1-C4)alkoxy;

$R_3$ is hydrogen or a group —$CH_2R_6$;

$R_4$ and $R_5$ are each independently a hydrogen, a (C1-C4) alkyl or a trifluoromethyl;

or else $R_4$ is hydrogen and $R_5$ and $w_6$ together constitute an ethylene or trimethylene radical; and $R_6$ is hydrogen, or when the substituents $g_2$, $g_3$, $g_4$, $g_5$ and/or $g_6$ are other than a (C1-C4)alkyl, $R_6$ is hydrogen, a (C1-C4)alkyl, a fluorine, a hydroxyl, a (C1-C5)alkoxy, a (C1-

C5)alkylthio, a hydroxy(C1-C5)alkoxy, a cyano, a (C1-C5) alkylsulfinyl or a (C1-C5)alkylsulfonyl;

and its salts.

CB2 receptor antagonists have also been described in the international patent publication WO 98/31227. Accordingly, use may be made also of compounds of formula (VI):

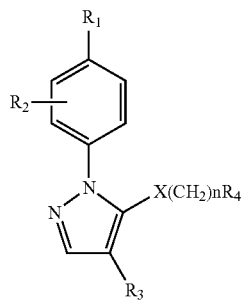

wherein:

$R_1$ is $OCH_3$, Br, isopropyl, or Ar;

$R_2$ is H, OH, (C1-C5)alkoxy, (C1-C5)alkyl, $N(R_5)_2$, $NO_2$, Br, F, I, Cl, $CF_3$, or $X(C(R_5)_2)OR_5$;

$R_3$ is hydrogen, $(CH_2)_nXR_5$, $C(O)R_5$, $CO_2R_5$, $CON(R_5)_2$, oxazolinyl, oxazolyl, thiazolyl, pyrazolyl, triazolyl, imidazolyl, tetrazolyl, imidazolinyl, thiazolinyl, isoxazolyl, oxadiazolyl, or thiadiazolyl, each of these heterocyclic rings being unsubstituted or substituted by one or two (C1-C3) alkyl or fluoroalkyl groups;

$R_4$ is morpholinyl, piperazinyl or piperidinyl, each moiety being unsubstituted or substituted by one or two (C1-C5) alkyl, OH, $NO_2$ or $N(R_5)_2$ groups;

$R_5$ is hydrogen or (C1-C8)alkyl;

X is O or $NR_6$;

Ar is phenyl, anthracenyl, naphthyl, indolyl, pyridinyl, thiophenyl, thiazolyl, isothiazolyl, triazolyl, tetrazolyl, imidazolyl, oxadiazolyl, pyrrolyl or pyrimidinyl; each moiety being unsubstituted or substituted by one or two Z groups;

Z is H, OH, $CO_2R_5$, (C1-C10)alkoxy, (C1-C5)alkyl, $N(R_5)_2$, $NO_2$, Br, F, I, Cl, $CF_3$, or $X(CH_2)_nOR_5$; and n is 1 to 6; and pharmaceutically acceptable salts thereof;

provided that when n is 1, $R_5$ is not hydrogen in $X(CH_2)_n OR_5$.

It may be preferred that when the CB2 receptor antagonist has the formula (VI) then said obesity-related disorder is not an immunologically mediated inflammatory disease, in particular is not diabetes, specifically not type I diabetes.

In another embodiment the CB2 receptor antagonist may consist in an antibody or antibody fragment that can partially or completely block CB2 activation (i.e. a partial or complete CB2 receptor blocking antibody or antibody fragment).

In particular, the CB2 receptor antagonist may consist in an antibody directed against the CB2 receptor, in such a way that said antibody impairs the binding of a CB2 ligand to said receptor.

Antibodies directed against the CB2 receptor can be raised according to known methods by administering the appropriate antigen or epitope to a host animal selected, e.g., from pigs, cows, horses, rabbits, goats, sheep, and mice, among others. Various adjuvants known in the art can be used to enhance antibody production. Although antibodies useful in practicing the invention can be polyclonal, monoclonal antibodies are preferred. Monoclonal antibodies against CB2 receptor or ligands of CB2 receptors can be prepared and isolated using any technique that provides for the production of antibody molecules by continuous cell lines in culture. Techniques for production and isolation include but are not limited to the hybridoma technique originally described by Kohler and Milstein (1975); the human B-cell hybridoma technique (Cote et al., 1983); and the EBV-hybridoma technique (Cole et al. 1985). Alternatively, techniques described for the production of single chain antibodies (see, e.g., U.S. Pat. No. 4,946,778) can be adapted to produce anti-CB2, or anti-CB2 ligands single chain antibodies. CB2 receptor antagonists useful in practicing the present invention also include anti-CB2, or anti-CB2 ligands antibody fragments including but not limited to F(ab')$_2$ fragments, which can be generated by pepsin digestion of an intact antibody molecule, and Fab fragments, which can be generated by reducing the disulfide bridges of the F(ab')$_2$ fragments. Alternatively, Fab and/or scFv expression libraries can be constructed to allow rapid identification of fragments having the desired specificity to CB2 receptor.

Humanized anti-CB2 or anti-CB2 ligands antibodies and antibody fragments therefrom can also be prepared according to known techniques. "Humanized antibodies" are forms of non-human (e.g., rodent) chimeric antibodies that contain minimal sequence derived from non-human immunoglobulin. For the most part, humanized antibodies are human immunoglobulins (recipient antibody) in which residues from a hypervariable region (CDRs) of the recipient are replaced by residues from a hypervariable region of a non-human species (donor antibody) such as mouse, rat, rabbit or nonhuman primate having the desired specificity, affinity and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. Methods for making humanized antibodies are described, for example, by Winter (U.S. Pat. No. 5,225,539) and Boss (Celltech, U.S. Pat. No. 4,816,397).

In still another embodiment, use may be made of aptamers.

Aptamers are a class of molecule that represents an alternative to antibodies in term of molecular recognition. Aptamers are oligonucleotide or oligopeptide sequences with the capacity to recognize virtually any class of target molecules with high affinity and specificity. Such ligands may be isolated through Systematic Evolution of Ligands by EXponential enrichment (SELEX) of a random sequence library, as described in Tuerk C. and Gold L., 1990. The random sequence library is obtainable by combinatorial chemical synthesis of DNA. In this library, each member is a linear oligomer, eventually chemically modified, of a unique sequence. Possible modifications, uses and advantages of this class of molecules have been reviewed in Jayasena S. D., 1999. Peptide aptamers consists of a conformationally constrained antibody variable region displayed by a platform protein, such as *E. coli* Thioredoxin A that are selected from combinatorial libraries by two hybrid methods (Colas et al., 1996).

Another aspect of the invention relates to the use of a selective inhibitor of CB2 receptor expression.

Thus, the invention provides the use of a selective inhibitor of CB2 receptor expression for the manufacture of a medicament intended for treating and/or preventing obesity and obesity-related disorder.

CB1 and CB2 receptor sequences showing low sequence identity, the inhibitors of CB2 receptor expression which may be used according to the invention advantageously provides selective inhibition of CB2 receptor expression, by comparison with CB1 receptor expression.

Inhibitors of CB2 receptor expression for use in the present invention may be based on anti-sense oligonucleotide constructs. Anti-sense oligonucleotides, including anti-sense RNA molecules and anti-sense DNA molecules, would act to directly block the translation of CB2 receptor mRNA by binding thereto and thus preventing protein translation or increasing mRNA degradation, thus decreasing the level of CB2 receptors, and thus activity, in a cell. For example, anti-sense oligonucleotides of at least about 15 bases and complementary to unique regions of the mRNA transcript sequence encoding CB2 receptor can be synthesized, e.g., by conventional phosphodiester techniques and administered by e.g., intravenous injection or infusion. Methods for using anti-sense techniques for specifically inhibiting gene expression of genes whose sequence is known are well known in the art (e.g. see U.S. Pat. Nos. 6,566,135; 6,566,131; 6,365,354; 6,410,323; 6,107,091; 6,046,321; and 5,981,732).

Small inhibitory RNAs (siRNAs) can also function as inhibitors of CB2 receptor expression for use in the present invention. CB2 receptor expression can be reduced by contacting a subject or cell with a small double stranded RNA (dsRNA), or a vector or construct causing the production of a small double stranded RNA, such that CB2 receptor expression is specifically inhibited (i.e. RNA interference or RNAi). Methods for selecting an appropriate dsRNA or dsRNA-encoding vector are well known in the art for genes whose sequence is known (e.g. see Tuschl, T. et al. (1999); Elbashir, S. M. et al. (2001); Hannon, G J. (2002); McManus, M T. et al. (2002); Brummelkamp, T R. et al. (2002); U.S. Pat. Nos. 6,573,099 and 6,506,559; and International Patent Publication Nos. WO 01/36646, WO 99/32619, and WO 01/68836).

Ribozymes can also function as inhibitors of CB2 receptor expression for use in the present invention. Ribozymes are enzymatic RNA molecules capable of catalyzing the specific cleavage of RNA. The mechanism of ribozyme action involves sequence specific hybridization of the ribozyme molecule to complementary target RNA, followed by endonucleolytic cleavage. Engineered hairpin or hammerhead motif ribozyme molecules that specifically and efficiently catalyze endonucleolytic cleavage of CB2 receptor mRNA sequences are thereby useful within the scope of the present invention. Specific ribozyme cleavage sites within any potential RNA target are initially identified by scanning the target molecule for ribozyme cleavage sites, which typically include the following sequences, GUA, GUU, and GUC. Once identified, short RNA sequences of between about 15 and 20 ribonucleotides corresponding to the region of the target gene containing the cleavage site can be evaluated for predicted structural features, such as secondary structure, that can render the oligonucleotide sequence unsuitable. The suitability of candidate targets can also be evaluated by testing their accessibility to hybridization with complementary oligonucleotides, using, e.g., ribonuclease protection assays.

Both antisense oligonucleotides and ribozymes useful as inhibitors of CB2 receptor expression can be prepared by known methods. These include techniques for chemical synthesis such as, e.g., by solid phase phosphoramadite chemical synthesis. Alternatively, anti-sense RNA molecules can be generated by in vitro or in vivo transcription of DNA sequences encoding the RNA molecule. Such DNA sequences can be incorporated into a wide variety of vectors that incorporate suitable RNA polymerase promoters such as the T7 or SP6 polymerase promoters. Various modifications to the oligonucleotides of the invention can be introduced as a means of increasing intracellular stability and half-life. Possible modifications include but are not limited to the addition of flanking sequences of ribonucleotides or deoxyribonucleotides to the 5' and/or 3' ends of the molecule, or the use of phosphorothioate or 2'-O-methyl rather than phosphodiesterase linkages within the oligonucleotide backbone.

Antisense oligonucleotides siRNAs and ribozymes of the invention may be delivered in vivo alone or in association with a vector. In its broadest sense, a "vector" is any vehicle capable of facilitating the transfer of the antisense oligonucleotide siRNA or ribozyme nucleic acid to the cells and preferably cells expressing CB2 receptor. Preferably, the vector transports the nucleic acid to cells with reduced degradation relative to the extent of degradation that would result in the absence of the vector. In general, the vectors useful in the invention include, but are not limited to, plasmids, phagemids, viruses, other vehicles derived from viral or bacterial sources that have been manipulated by the insertion or incorporation of the antisense oligonucleotide siRNA or ribozyme nucleic acid sequences. Viral vectors are a preferred type of vector and include, but are not limited to nucleic acid sequences from the following viruses: retrovirus, such as moloney murine leukemia virus, harvey murine sarcoma virus, murine mammary tumor virus, and rouse sarcoma virus; adenovirus, adeno-associated virus; SV40-type viruses; polyoma viruses; Epstein-Barr viruses; papilloma viruses; herpes virus; vaccinia virus; polio virus; and RNA virus such as a retrovirus. One can readily employ other vectors not named but known to the art.

Preferred viral vectors are based on non-cytopathic eukaryotic viruses in which non-essential genes have been replaced with the gene of interest. Non-cytopathic viruses include retroviruses (e.g., lentivirus), the life cycle of which involves reverse transcription of genomic viral RNA into DNA with subsequent proviral integration into host cellular DNA. Retroviruses have been approved for human gene therapy trials. Most useful are those retroviruses that are replication-deficient (i.e., capable of directing synthesis of the desired proteins, but incapable of manufacturing an infectious particle). Such genetically altered retroviral expression vectors have general utility for the high-efficiency transduction of genes in vivo. Standard protocols for producing replication-deficient retroviruses (including the steps of incorporation of exogenous genetic material into a plasmid, transfection of a packaging cell line with plasmid, production of recombinant retroviruses by the packaging cell line, collection of viral particles from tissue culture media, and infection of the target cells with viral particles are provided in Kriegler, 1990 and in Murry, 1991).

Preferred viruses for certain applications are the adenoviruses and adeno-associated viruses, which are double-stranded DNA viruses that have already been approved for human use in gene therapy. The adeno-associated virus can be engineered to be replication deficient and is capable of infecting a wide range of cell types and species. It further has advantages such as, heat and lipid solvent stability; high transduction frequencies in cells of diverse lineages, including hemopoietic cells; and lack of superinfection inhibition thus allowing multiple series of transductions. Reportedly, the adeno-associated virus can integrate into human cellular DNA in a site-specific manner, thereby minimizing the possibility of insertional mutagenesis and variability of inserted gene expression characteristic of retroviral infection. In addition, wild-type adeno-associated virus infections have been followed in tissue culture for greater than 100 passages in the absence of selective pressure, implying that the adeno-associated virus genomic integration is a relatively stable event. The adeno-associated virus can also function in an extrachromosomal fashion.

Other vectors include plasmid vectors. Plasmid vectors have been extensively described in the art and are well known to those of skill in the art. See e.g. Sambrook et al., 1989. In the last few years, plasmid vectors have been used as DNA vaccines for delivering antigen-encoding genes to cells in vivo. They are particularly advantageous for this because they do not have the same safety concerns as with many of the viral vectors. These plasmids, however, having a promoter compatible with the host cell, can express a peptide from a gene operatively encoded within the plasmid. Some commonly used plasmids include pBR322, pUC18, pUCl9, pRC/CMV, SV40, and pBlueScript. Other plasmids are well known to those of ordinary skill in the art. Additionally, plasmids may be custom designed using restriction enzymes and ligation reactions to remove and add specific fragments of DNA. Plasmids may be delivered by a variety of parenteral, mucosal and topical routes. For example, the DNA plasmid can be injected by intramuscular, intradermal, subcutaneous, or other routes. It may also be administered by intranasal sprays or drops, rectal suppository and orally. It may also be administered into the epidermis or a mucosal surface using a gene-gun. The plasmids may be given in an aqueous solution, dried onto gold particles or in association with another DNA delivery system including but not limited to liposomes, dendrimers, cochleate and microencapsulation.

Another object of the invention relates to a method for treating and/or preventing obesity and/or obesity-related disorders comprising administering a subject in need thereof with a selective inhibitor of CB2 expression and/or activity, as above described.

The selective inhibitor of CB2 receptor activity and/or expression may be administered in the form of a pharmaceutical composition, as defined below.

Preferably, said inhibitor is administered in a therapeutically effective amount.

By a "therapeutically effective amount" is meant a sufficient amount of the CB2 receptor antagonist or inhibitor of CB2 expression to treat and/or to prevent obesity and/or obesity-related disorders at a reasonable benefit/risk ratio applicable to any medical treatment.

It will be understood that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed, the age, body weight, general health, sex and diet of the patient; the time of administration, route of administration, and rate of excretion of the specific compound employed; the duration of the treatment; drugs used in combination or coincidential with the specific polypeptide employed; and like factors well known in the medical arts. For example, it is well within the skill of the art to start doses of the compound at levels lower than those required to achieve the desired therapeutic effect and to gradually increase the dosage until the desired effect is achieved. However, the daily dosage of the products may be varied over a wide range from 0.01 to 1,000 mg per adult per day. Preferably, the compositions contain 0.01, 0.05, 0.1, 0.5, 1.0, 2.5, 5.0, 10.0, 15.0, 25.0, 50.0, 100, 250 and 500 mg of the active ingredient for the symptomatic adjustment of the dosage to the patient to be treated. A medicament typically contains from about 0.01 mg to about 500 mg of the active ingredient, preferably from 1 mg to about 100 mg of the active ingredient. An effective amount of the drug is ordinarily supplied at a dosage level from 0.0002 mg/kg to about 20 mg/kg of body weight per day, especially from about 0.001 mg/kg to 7 mg/kg of body weight per day.

Screening Methods

Inhibitors of the invention can be further identified by screening methods described in the state of the art. The screening methods of the invention can be carried out according to known methods.

The screening method may measure the binding of a candidate compound to the receptor, or to cells or membranes bearing the receptor, or a fusion protein thereof by means of a label directly or indirectly associated with the candidate compound. Alternatively, a screening method may involve measuring or, qualitatively or quantitatively, detecting the competition of binding of a candidate compound to the receptor with a labelled competitor (e.g., antagonist or agonist). Further, screening methods may test whether the candidate compound results in a signal generated by an antagonist of the receptor, using detection systems appropriate to cells bearing the receptor. Antagonists can be assayed in the presence of a known agonist (e.g., DELTA-9-THC, WIN 55212-2 or CP 55940) and an effect on activation by the agonist by the presence of the candidate compound is observed. Further, screening methods may comprise the steps of mixing a candidate compound with a solution comprising a CB2, to form a mixture, and measuring the activity in the mixture, and comparing to a control mixture which contains no candidate compound. Competitive binding using known agonist such DELTA-9-THC, WIN 55212-2 or CP 55940 is also suitable.

The antagonistic activity of the candidate compounds towards the CB2 receptor may be for example determined using various models. For example, it is known that CB2 receptor agonists (DELTA-9-THC, WIN 55212-2 or CP 55940) are capable of inhibiting the adenylate cyclase activity induced by Forskolin as described by M. Rinaldi-Carmona et al (1996). Thus in this model, one may test the ability of said candidate compound to block the effect of the CB2 receptor agonists.

Pharmaceutical Compositions

The CB2 receptor antagonist or inhibitor of CB2 receptor expression may be combined with pharmaceutically acceptable excipients, and optionally sustained-release matrices, such as biodegradable polymers, to form therapeutic compositions.

In the pharmaceutical compositions of the present invention for oral, sublingual, subcutaneous, intramuscular, intravenous, transdermal, local or rectal administration, the active principle, alone or in combination with another active principle, can be administered in a unit administration form, as a mixture with conventional pharmaceutical supports, to animals and human beings. Suitable unit administration forms comprise oral-route forms such as tablets, gel capsules, powders, granules and oral suspensions or solutions, sublingual and buccal administration forms, aerosols, implants, subcutaneous, transdermal, topical, intraperitoneal, intramuscular, intravenous, subdermal, transdermal, intrathecal and intranasal administration forms and rectal administration forms.

Preferably, the pharmaceutical compositions contain vehicles which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi.

Solutions comprising compounds of the invention as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The CB2 receptor antagonist or inhibitor of CB2 receptor expression of the invention can be formulated into a composition in a neutral or salt form. Pharmaceutically acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetables oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin.

Sterile injectable solutions are prepared by incorporating the active polypeptides in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion. Some variation in dosage will necessarily occur depending on the condition of the subject being treated. The person responsible for administration will, in any event, determine the appropriate dose for the individual subject.

The CB2 receptor antagonist or inhibitor of CB2 receptor expression of the invention may be formulated within a therapeutic mixture to comprise about 0.0001 to 1.0 milligrams, or about 0.001 to 0.1 milligrams, or about 0.1 to 1.0 or even about 10 milligrams per dose or so. Multiple doses can also be administered.

In addition to the compounds of the invention formulated for parenteral administration, such as intravenous or intramuscular injection, other pharmaceutically acceptable forms include, e.g. tablets or other solids for oral administration; liposomal formulations; time release capsules; and any other form currently used.

The invention will further be illustrated in view of the following examples.

EXAMPLE 1

Methods

Animals and Experimental Design: The generation of mice with a targeted mutation of the CB2 gene on a mixed genetic background has been described previously (Buckley, N. E et al. 2000). Wild type C57BL/6, ob/ob and ob/ob+ mice were obtained from Janvier (France).

Adult male mice (7-10 week-old) were housed under 12 hours of light/12 hours of dark cycle, in a temperature-controlled environment. Wild type mice (WT) and CB2−/− mice were fed either standard chow (TD 2016, Harlan) or high fat diet (36% fat, TD 99249, Harlan) for 15 weeks. Body weight and food intake were measured weekly. Mice were scarified after overnight fasting. All experimental protocols were conducted in accordance with French government policies (Services vétérinaires de la Santé et de la production animale, Ministère français de l'Agriculture).

At the time of sacrifice, brown and white (subcutaneaous inguinal (SAT) and epididymal (EAT)) adipose tissues were removed, weighed and snap frozen in liquid nitrogen. Liver samples were taken from several lobes and either fixed in buffered formalin, or snap frozen in liquid nitrogen in RNA later (Qiagen). All samples were stored at −80° C. until use.

Tissue and serum analysis: Blood was collected at the time mice were sacrificed, after overnight fasting. Glycemia was determinated by Accu-Check active bands (Roche Diagnostics) and insulinemia was quantified by Elisa (Ultrasensitive mouse sensitive Elisa, Mercodia). Serum concentrations of leptin were measured by commercial ELISA assays (Quantikine Elisa kit, R&D). Hepatic triglycerides were extracted from 50 mg of liver homogenates in 10 ml of isopropanol, and quantitated using a triglyceride determination kit (Sigma).

RNA preparation and RT-PCR: Total RNA was extracted from liver and white adipose tissues, using RNeasy® Lipid Tissue Mini kit (QIAGEN). Quantitative RT-PCR was carried out on a Light Cycler (Roche Diagnostics), as previously described (Julien B. et al. 2005). Oligonucleotide primer sequences of the genes studied are listed in Table 1.

TABLE 1

Sequence of primers used for RT-PCR

| Target (Genbank Accession Number) | Primer Sequence | PCR product (size) |
|---|---|---|
| 18S (X00686) | sense 5'-GTAACCCGTTGAACCCCATT-3' (SEQ ID NO: 1) | 151 bp |
| | antisense: 5'-CCATCCAATCGGTAGTAGCG-3' (SEQ ID NO: 2) | |
| CB1 (NM_007726) | sense 5'-GGGCAAATTTCCTTGTAGCA-3' (SEQ ID NO: 3) | 182 bp |
| | antisense 5'-TCTGCAAGGCCGTCTAAGAT-3' (SEQ ID NO: 4) | |
| CB2 (NM_009924) | sense 5'-GGATACAGAATAGCCAGGAC-3' (SEQ ID NO: 5) | 148 bp |
| | antisense 5'-GGAGCCGTTGGTCACTTCTG-3' (SEQ ID NO: 6) | |
| MCP-1 (NM_011333) | sense 5'-GGGCCTGCTGTTCACAGTT-3' (SEQ ID NO: 7) | 121 bp |
| | antisense 5'-CCAGCCTACTCATTGGGAT-3' (SEQ ID NO: 8) | |
| F4/80 (NM_010130) | sense 5'-CTTTGGCTATGGGCTTCCAGTC-3' (SEQ ID NO: 9) | 165 bp |
| | antisense 5'-GCAAGGAGGACAGAGTTTATCGTG-3' (SEQ ID NO: 10) | |
| TNF-alpha (NM_013693) | sense 5'-AATGGCCTCCCTCTCATCAGTT-3' (SEQ ID NO: 11) | 164 bp |
| | antisense 5'-CCACTTGGTGGTTTGCTACGA-3' (SEQ ID NO: 12) | |
| IL-6 (NM_031168) | sense 5'-GAACAACGATGATGCACTTGC-3' (SEQ ID NO: 13) | 144 bp |
| | antisense 5'-TCCAGGTAGCTATGGTACTCC-3' (SEQ ID NO: 14) | |
| SREBP-1c (NM_011480) | sense 5'-GAAGCGCTACCGGTCTTCTATCA-3' (SEQ ID NO: 15) | 212 bp |
| | antisense 5'-AAGCTGACACCAGGTCCTTCAGT-3' (SEQ ID NO: 16) | |
| ACC1 (NM_133360) | sense 5'-AACCTGGTGAAGCTGGACCTA-3' (SEQ ID NO: 17) | 203 bp |
| | antisense 5'-GCCACAGTGAAATCTCGTTG-3' (SEQ ID NO: 18) | |
| Leptin (NM_008493) | sense 5'-CATCTGCTGGCCTTCTCCAA-3' (SEQ ID NO: 19) | 72 bp |
| | antisense 5'-ATCCAGGCTCTCTGGCTTCTG-3' (SEQ ID NO: 20) | |

The PCR amplified products were analyzed on a 2% agarose gel, and sequenced.

Liver and adipose tissue histology. Liver specimen were fixed in 10% formalin and paraffin-embedded. Tissue sections (4 µm) were stained with hematoxylin-eosin for routine examination. Adipocyte size was quantified on adipose tissue sections (8 µm) stained with hematoxylin-eosin. Quantification was performed on at least 30 cells from 3 separate fields in 7 WT and 5 CB2−/− HFD fed animals, using Image J software.

Statistics: Results are expressed as mean±SEM and were analyzed by either Mann and Whitney test, one way ANOVA or two way ANOVA followed by Bonferroni's test. $P<0.05$ was taken as the minimum level of significance.

Figure 1:
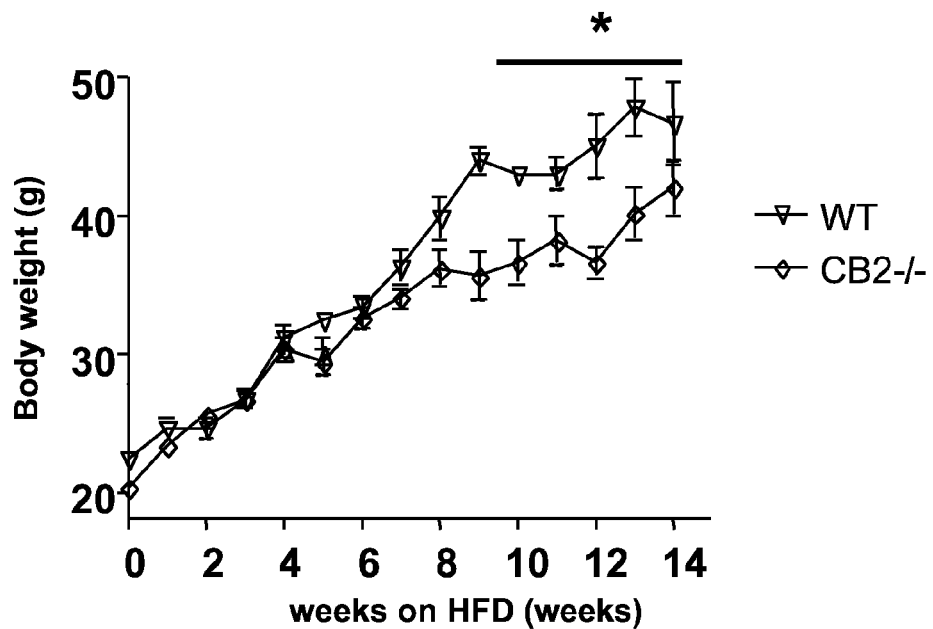
Figure 2:
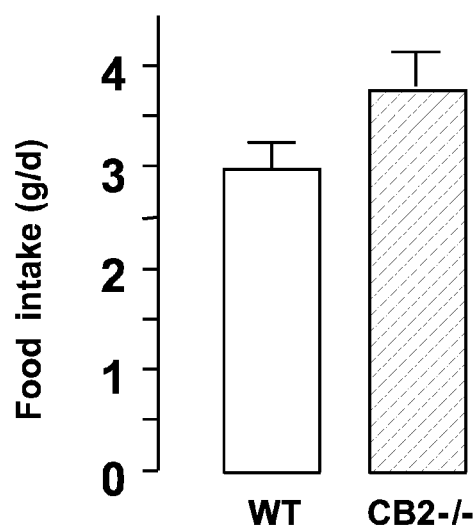

Results:

CB2−/− mice are resistant to diet-induced obesity: Wild type and CB2−/− mice were subjected to high fat diet (HFD) for 15 weeks, while respective controls remained on regular mouse chow. At the onset of the experiment, average weight was similar in both 22.2±0.13 g for WT and 20.1±0.4 g for CB2−/−. However, after 9 weeks of HFD, mean weight of CB2−/− mice was significantly lighter than that of their wild type counterparts, and by study completion CB2−/− animals weighed 28% less than wild type mice (41.6±1.3 g for CB2−/− vs 46.7±1.2 g for WT, p<0.05, FIG. 1), despite similar food intake (FIG. 2).

At the end of the study, the HFD fed CB2−/− mice had a significant reduction in white and brown adipose tissue weights (Table 2).

Figure 3:
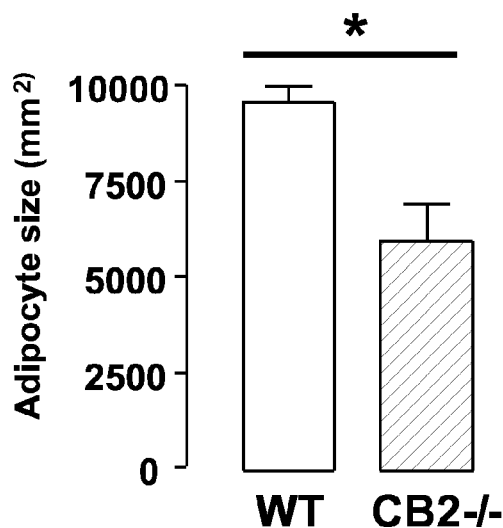

Furthermore, the adiposity index of CB2−/− mice (defined as total fat mass/eviscerated body weight×100) was significantly lower as compared to WT mice (Table 2). Finally, the adipocyte size of HFD-fed CB2−/− mice was significantly smaller than that of HFD-fed WT mice (FIG. 3).

Figure 4:
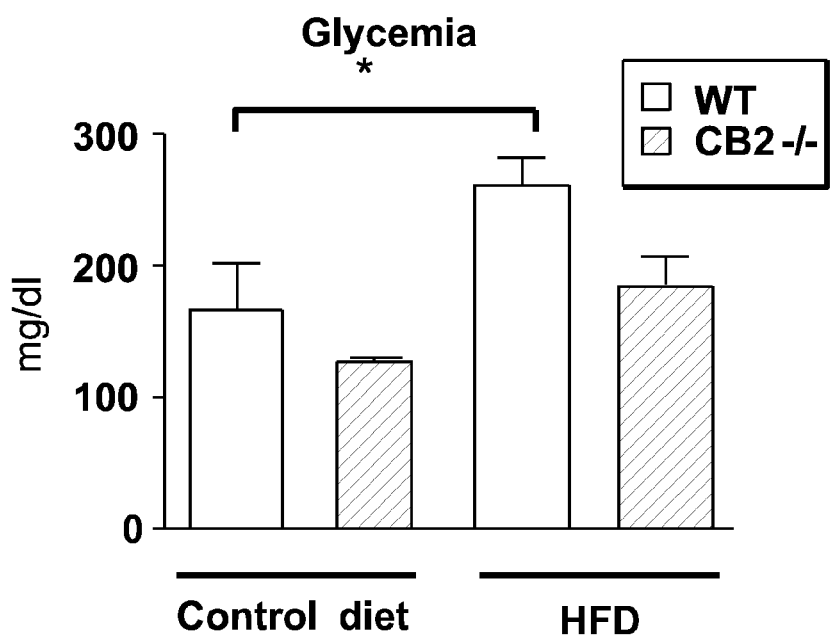
Figure 5:
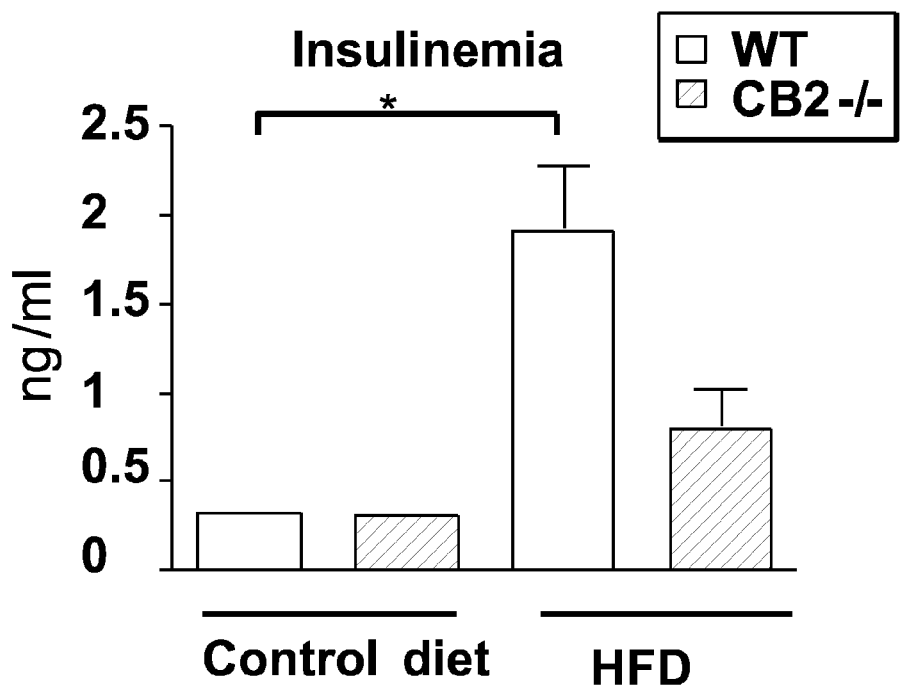
Figure 6:
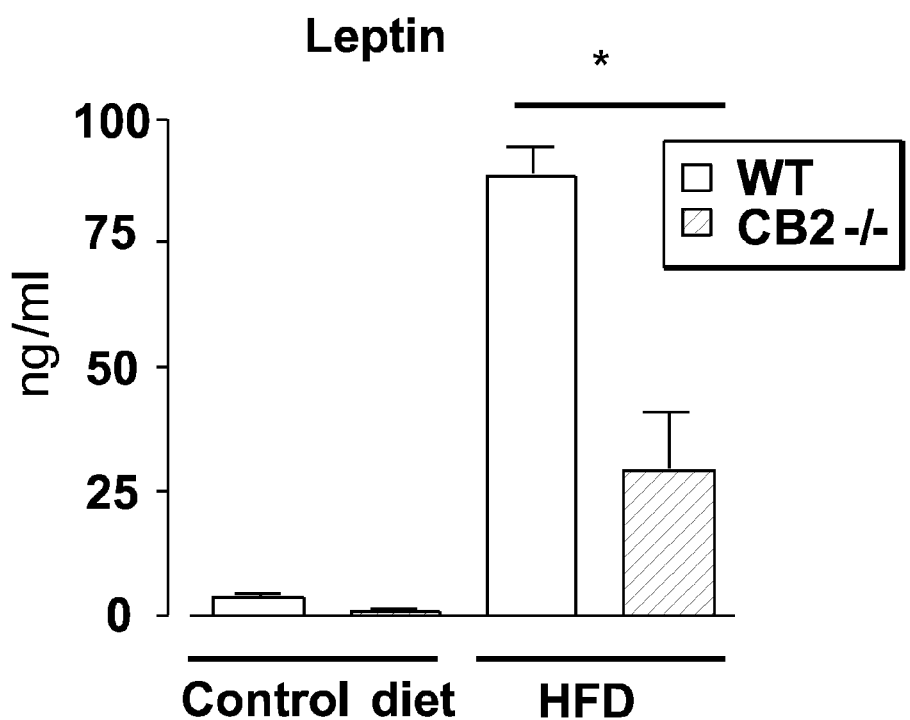
Figure 7:
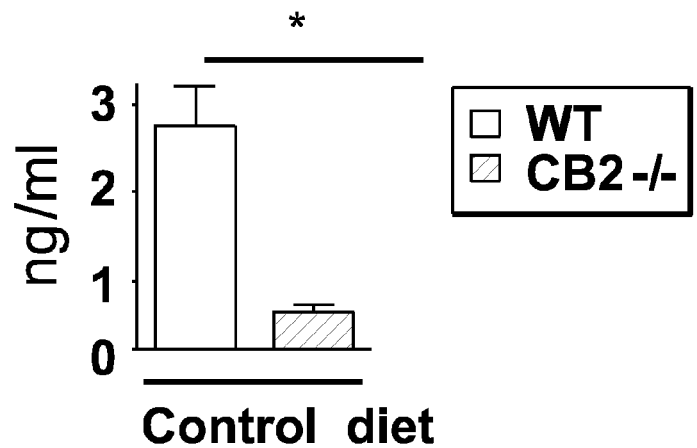
FIG. 7 shows serum leptin levels in WT and CB2-/- mice under control diet. *p<0.05 for WT vs CB2-/- HFD mice.

Wild type HFD-fed mice exhibited expected hormonal and metabolic changes, including hyperglycemia, hypermia and hyperleptinemia (FIGS. 4, 5 and 6). In contrast, in CB2−/− HFD-fed mice insulin and glucose serum levels remained within normal ranges (FIGS. 4 and 5), although differences between WT and CB2−/− mice did not reach significance. In addition, serum leptin levels were significantly lower in CB2−/− HFD-fed mice as well as in CB2−/− mice fed with control diet, as compared to their WT counterparts (FIG. 6).

Figure 8:
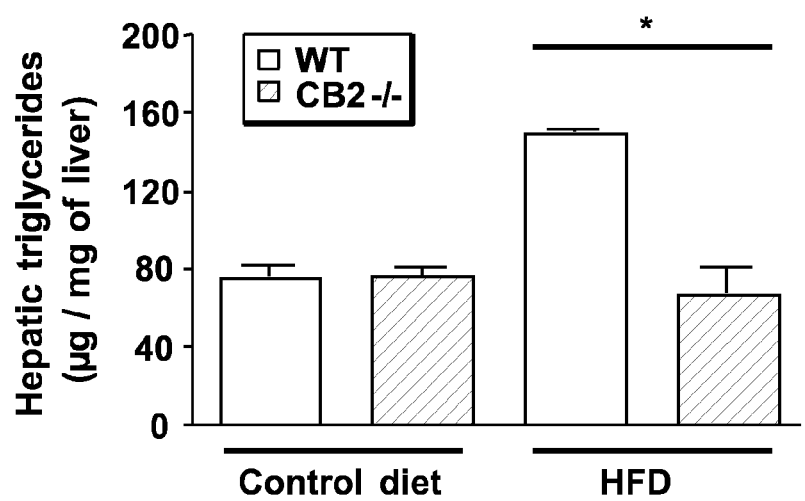
FIG. 8 shows hepatic triglycerides measured in WT and CB2-/- mice fed with control diet of high fat diet *p<0.05 for WT vs CB2-/- HFD mice.
Figure 9:
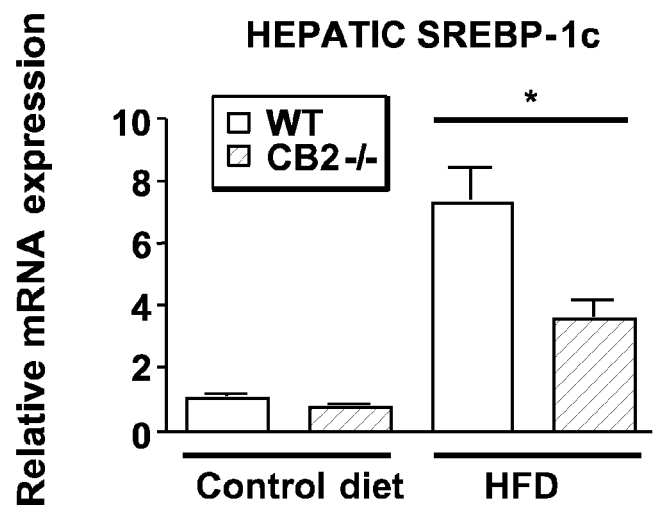
FIG. 9 shows hepatic expression of SREBP-1c mRNA in WT (n=7) and CB2-/- mice (n=5) fed a high fat diet. *p<0.05 for WT vs CB2-/- HFD mice.

CB2 invalidation blunts obesity-induced hepatic steatosis: As expected, obese WT mice developed fatty liver, as shown by histological analysis of liver tissue sections, and increased hepatic triglycerides (FIG. 8). In contrast, CB2−/− HFD-fed mice were protected from hepatic steatosis (FIG. 8). Accordingly, the induction of SREBP-1c and ACC1 was consistently lower in the liver of CB2−/− HFD-fed mice (FIG. 9).

Taken together these results unravel a novel role for CB2 in the pathogenesis of obesity, insulin resistance and hepatic steatosis induced by a high fat diet.

Regulation of CB receptor expression in liver and white adipose tissue in wild-type and CB2−/− mice under HFD: As expected, CB2−/− mice lacked the CB2 gene, and displayed normal CB1 gene expression (FIG. 10). In WT mice fed a HFD, CB2 receptor expression was induced by 29.8±5.0 fold in the EAT (Epidemial Adipose Tissue), but remained unchanged in the liver (FIG. 11). Similar results were obtained in ob/ob mice, with a 6.8±1.9 fold induction of CB2 receptor mRNA expression in the adipose tissue and no change in the liver (FIG. 11). CB1 receptor mRNA regulation was also investigated in WT and CB2−/− mice. As described by others (Cota D. et al. 2003; Osei-Hyiaman, D et al. 2005), CB1 receptor mRNA expression was induced in EAT and liver of HFD-fed WT mice by 2.68±0.35 and 3.57±0.96 fold, respectively (FIG. 12). In contrast, CB1 receptor mRNA was not induced in EAT and liver of HFD-fed CB2−/− mice (FIG. 12).

These results demonstrate that high fat diet up-regulates CB2 mRNA expression in EAT but not in the liver. In addition, they also show that CB1 receptor mRNA expression is controlled by CB2 receptors during HFD.

HFD-fed CB2−/− mice display reduced inflammation in EAT and liver. It is well recognized that adipose tissue is characterized by a low grade inflammatory state during obesity that may contribute to the development of insulin resistance. Adipocytes secrete several adipokines that contribute to macrophage infiltration into adipose tissue, and to subsequent development of insulin resistance and to hepatic steatosis. Recent data have shown that the expression of various inflammation-related proteins, including TNF-alpha and MCP-1 are up-regulated during diet-induced obesity, and play a key role in the pathogenesis of the metabolic syndrome and of the liver complications of obesity. As expected, EAT of HFD-fed wild type mice exhibited a strong induction of TNF-alpha and MCP-1 mRNA expressions, and an increased density of macrophages, as assayed by mRNA expression of F4/80, a specific marker of mature macrophages (FIG. 13). In contrast, inductions of TNF-alpha, MCP-1 and F4/80 were significantly lower in the EAT of HFD-fed CB2−/− mice (FIG. 13).

The consequences of CB2 invalidation on liver inflammation in HFD fed mice were also investigated. As observed in the adipose tissue, hepatic induction of TNF-alpha, MCP-1 and F4/80 mRNA was lower in HFD-fed CB2−/− mice compared to HFD-fed wild type mice (FIG. 14).

Therefore, these results demonstrate that CB2 receptor plays a major role in the inflammatory process underlying the development of obesity.

In summary, it is shown herein that CB2 receptor is over-expressed in the adipose tissue and plays a major role in the development of obesity, insulin resistance, inflammation and hepatic steatosis.

TABLE 2

Tissue weight and adiposity index (total fat mass/eviscerated body weight) of WT and CB2 −/− mice following 15 weeks of high fat diet

|  | Mice | EAT (mg) | SAT (mg) | adiposity index | BAT (mg) |
|---|---|---|---|---|---|
| Control Diet | WT (n = 13) | 309 ± 83 | 130 ± 28 | 2.2 ± 0.2 | 100 ± 1.5 |
|  | CB2−/− (n = 15) | 213 ± 37 | 103 ± 3 | 1.8 ± 0.1 | 98 ± 9 |
| High fat Diet | WT (n = 7) | 2472 ± 92* | 1791 ± 116* | 9.6 ± 0.4* | 226 ± 17* |
|  | CB2−/− (n = 5) | 1732 ± 207*$ | 774 ± 227*$ | 6.7 ± 0.7*$ | 111 ± 8*$ |

*$p < 0.05$ for HFD vs control diet;
$\$p < 0.05$ for HFD WT vs HFD CB2 −/− mice;
BAT (brown adiposetissue);
SAT (suscutaneus inguinal adipose tissue);
EAT (Epididymal adipose tissue)

EXAMPLE 2

Methods

Animals and Experimental Design: Experimental protocols were conducted in accordance with French government policies (Services véterinaires de la Santé et de la production animale, Ministère français de l'Agriculture). Animals were housed under 12 hours of light/12 hours of dark cycle, in a temperature-controlled environment. The impact of the CB2 antagonist AM630 was evaluated in 6 week-old male obese $Lep^{Ob}/Lep^{Ob}$ male mice (ob/ob) and lean $Lep^{Ob+}/Lep^{Ob}$ counterparts (ob+/ob). Mice received an 17 day-course of daily intraperitoneal injection of 1 mg/kg AM630 (n=10 ob/ob and n=5 ob+/ob) or vehicle (n=8 ob/ob and n=5 ob+/ob). AM630 (Tocris) was freshly dissolved in a vehicle solution containing 1 drop of Tween 80 in 0.1 ml dimethylsulfoxide (DMSO), sonicated, and further diluted 50 times in NaCl 9‰. Body weight and food intake were measured daily. Mice were sacrificed after overnight fasting. White epididymal adipose tissue was removed, weighed and either fixed in buffered formalin, or snap frozen in liquid nitrogen. All samples were stored at −80° C. until use.

RNA preparation and RT-PCR: Total RNA was extracted from mice epididymal fat using RNeasy® Lipid Tissue Mini kit (QIAGEN). Quantitative RT-PCR was carried out on a Light Cycler (Roche Diagnostics), as previously described. Oligonucleotide primer sequences of the mouse genes studied are listed in Table 3.

TABLE 3

Sequence of primers used for RT-PCR

| Target | Primer Sequence |
|---|---|
| mouse 18S | sense<br>5'-ACCAGAGCGAAAGCATTTGCCA3'<br>(SEQ ID NO: 21)<br><br>antisense:<br>5'-ATCGCCAGTCGGCATCGTTTAT-3'<br>(SEQ ID NO: 22) |
| mouse MCP-1 | sense<br>5'-GGGCCTGCTGTTCACAGTT-3'<br>(SEQ ID NO: 7)<br><br>antisense<br>5'-CCAGCCTACTCATTGGGAT-3'<br>(SEQ ID NO: 8) |
| mouse F4/80 | sense<br>5'-CTTTGGCTATGGGCTTCCAGTC-3'<br>(SEQ ID NO: 9)<br><br>antisense<br>5'-GCAAGGAGGACAGAGTTTATCGTG-3'<br>(SEQ ID NO: 10) |
| mouse TNF-αλπηα | sense<br>5'-AATGGCCTCCCTCTCATCAGTT-3'<br>(SEQ ID NO: 11)<br><br>antisense<br>5'-CCACTTGGTGGTTTGCTACGA-3'.<br>(SEQ ID NO: 12) |

The PCR amplified products were analyzed on a 2% agarose gel, and sequenced.

Results:

A number of studies have established that obesity is associated with a low-grade inflammation in the adipose tissue that contributes to the development of systemic insulin resistance and fatty liver. It has also been shown that macrophages accumulate in the adipose tissue during obesity and contribute to this inflammatory state.

Regulation and distribution of CB2 receptors in adipose tissue were further characterized in two experimental models of obesity (FIG. 15a). Interestingly, HFD-fed wild type mice and ob/ob mice showed a strong induction of CB2 mRNA that correlated with body weight gain (FIG. 15a, left panel). CB2 receptor mRNA was undetectable in adipocytes as well as in 3T3-L1 preadipocytes, and was strongly induced in the stromal vascular fraction of epididymal adipose tissue prepared from obese (ob/ob) mice as compared to lean (ob+/ob−) animals (FIG. 15a, right panel), indicating macrophage-related expression of the CB2 receptor. As expected, the adipose tissue of obese HFD-fed WT mice was significantly infiltrated by macrophages, as shown by the strong induction of the mRNA encoding the macrophage-related marker F4/80 (FIG. 15b, left panel), and by the accumulation of F4/80 positive cells in crown clusters around adipocytes (FIG. 15b, right panel). This increase in macrophage density was associated with a marked induction of TNF-alpha and MCP-1 mRNA expressions, reflecting the inflammatory response of fat tissue in obese WT animals (FIG. 15c). In contrast, genetical inactivation of CB2 was associated to a lesser degree of macrophage accumulation in fat tissue (FIG. 15b) and to a marked decrease in the inflammatory response, as assessed by TNF-alpha and MCP-1 mRNA expressions (FIG. 15c).

In order to comfort data obtained in genetically deficient CB2−/− mice, pharmacological inhibition of CB2 was induced by daily intraperitoneal administration of the CB2 antagonist AM630 (1 mg/kg over 17 days) to six week-old ob/ob mice. AM 630 reduced fat inflammatory response in obese mice, as shown by a lesser induction of F4/80, TNF-alpha and MCP-1 mRNAs (FIG. 16).

In aggregate, these results indicate that, in this animal model, CB2 antagonism is associated with a reduced inflammatory response in the adipose tissue, and may thereby ameliorate insulin resistance and steatosis.

REFERENCES

The following references are incorporated by reference in their entirety:

Barth F, Rinaldi-Carmona M. The development of cannabinoid antagonists. Curr Med Chem. 1999 August; 6(8):745-55.

Bray G A, Blackburn G L, Ferguson J M, Greenway F L, Jain A K, Mendel C M, Mendels J, Ryan D H, Schwartz S L, Scheinbaum M L, Seaton T B. Sibutramine produces dose-related weight loss. Obes Res. 1999 March; 7(2):189-98.

Brummelkamp T R, Bernards R, Agami R. A system for stable expression of short interfering RNAs in mammalian cells. Science. 2002 Apr. 19; 296(5567):550-3.

Buckley, N. E., McCoy, K. L., Mezey, E., Bonner, T., Zimmer, A., Felder, C. C., Glass, M., and Zimmer, A. (2000) Eur J Pharmacol 396, 141-149.

Carter P, Bedouelle H, Winter G. Improved oligonucleotide site-directed mutagenesis using M13 vectors. Nucleic Acids Res. 1985 Jun. 25; 13(12):4431-43.

Charalambous A, Yan G, Houston D B, Howlett A C, Compton D R, Martin B R, Makriyannis A. 5'-Azido-delta 8-THC: a novel photoaffinity label for the cannabinoid receptor. J Med Chem. 1992 Aug. 7; 35(16):3076-9.

Cheng Y, Prusoff W H, Relationship between the inhibition constant (Ki) and the concentration of inhibitor which causes 50 percent inhibition (150) of an enzymatic reaction, Biochem Pharmacol. 1973 Dec. 1; 22(23):3099-108.

Colas P, Cohen B, Jessen T, Grishina I, McCoy J, Brent R. (1996) Genetic selection of peptide aptamers that recognize and inhibit cyclin-dependent kinase 2. Nature, 380, 548-50.

Cole et al., Monoclonal Antibodies and Cancer Therapy, Alan R. Liss, Inc., 1985, pp. 77-96).

Cota, D., Marsicano, G., Tschop, M., Grubler, Y., Flachskamm, C., Schubert, M., Auer, D., Yassouridis, A., Thone-Reineke, C., Ortmann, S., Tomassoni, F., Cervino, C., Nisoli, E., Linthorst, A. C., Pasquali, R., Lutz, B., Stalla, G. K., and Pagotto, U. (2003) J Clin Invest 112, 423-431.

Cote R J, Morrissey D M, Houghton A N, Beattie E J Jr, Oettgen H F, Old L J. Generation of human monoclonal antibodies reactive with cellular antigens. Proc Natl Acad Sci USA. 1983 April; 80(7):2026-30.

Davidson M H, Hauptman J, DiGirolamo M, Foreyt J P, Halsted C H, Heber D, Heimburger D C, Lucas C P, Robbins D C, Chung J, Heymsfield S B. Weight control and risk factor reduction in obese subjects treated for 2 years with orlistat: a randomized controlled trial. JAMA. 1999 Jan. 20; 281(3):235-42.

De Lean A, Munson P J, Rodbard D. Mol Pharmacol. 1979 January; 15(1):60-70.

Després J P, Golay A, Sjöström L; for the Rimonabant in Obesity-Lipids Study Group. Effects of rimonabant on metabolic risk factors in overweight patients with dyslipidemia. N Engl J Med. 2005; 353:2121-2134.

Devane W A, Dysarz F A 3rd, Johnson M R, Melvin L S, Howlett A C. Determination and characterization of a cannabinoid receptor in rat brain. Mol Pharmacol. 1988 November; 34(5):605-13.

Dodd P R, Hardy J A, Oakley A E, Edwardson J A, Perry E K, Delaunoy J P. A rapid method for preparing synaptosomes: comparison, with alternative procedures. Brain Res. 1981 Dec. 7; 226(1-2):107-18.

Douglas A, Douglas J G, Robertson C E, Munro J F. Plasma phentermine levels, weight loss and side-effects. Int J Obes. 1983; 7(6):591-5.

Elbashir S M, Harborth J, Lendeckel W, Yalcin A, Weber K, Tuschl T. Duplexes of 21-nucleotide RNAs mediate RNA interference in cultured mammalian cells. Nature. 2001 May 24; 411(6836):494-8.

Farell G C. Non-alcoholic steatohepatitis: what is it, and why is it important in the Asia-Pacific region? J Gastroenterol Hepatol 2003; 18:124-138.

Ford E S, Giles W H, Dietz W H. Prevalence of the metabolic syndrome among US adults: findings from the third National Health and Nutrition Examination Survey. JAMA. 2002 Jan. 16; 287(3):356-9.

Guy-Grand B, Apfelbaum M, Crepaldi G, Gries A, Lefebvre P, Turner P. International trial of long-term dexfenfluramine in obesity. Lancet. 1989 Nov. 11; 2(8672):1142-5.

Hannon G J. RNA interference. Nature. 2002 Jul. 11; 418 (6894):244-51.

Hosohata Y, Quock R M, Hosohata K, Makriyannis A, Consroe P, Roeske W R, Yamamura H I. AM630 antagonism of cannabinoid-stimulated [$^{35}$S]GTP gamma S binding in the mouse brain. Eur J Pharmacol. 1997 Feb. 19; 321(1):R1-3.

Iwamura, H, et al., 2001, "In Vitro and In Vivo Pharmacological Characterization of JTE-907, a Novel Selective Ligand for Cannabinoid CB2 Receptor," Journal of Pharmacology and Experimental Therapeutics, Vol. 296, No. 2, pp. 420-425.

Jayasena S. D. (1999) Aptamers: an emerging class of molecules that rival antibodies in diagnostics. Clin Chem. 45(9):1628-50.

Julien, B., Grenard, P., Teixeira-Clerc, F., Tran-Van-Nhieu, J., Li, L., Karzak, M., Zimmer, A., Mallat, A., and Lotersztajn, S. (2005) Gastroenterology 128, 742-755.

Kohler G, Milstein C. Continuous cultures of fused cells secreting antibody of predefined specificity. Nature. 1975 Aug. 7; 256(5517):495-7.

Kriegler, A Laboratory Manual," W.H. Freeman C.O., New York, 1990.

Matsuda et al., 1990 Nature (Lond) 346: 561-564

McManus M T, Sharp P A. Gene silencing in mammals by small interfering RNAs. Nat Rev Genet. 2002 October; 3(10): 737-47.

Murry, "Methods in Molecular Biology," vol. 7, Humana Press, Inc., Cliffton, N.J., 1991.

Osei-Hyiaman, D., Depetrillo, M., Pacher, P., Liu, J., Radaeva, S., Batkai, S., Harvey-White, J., Mackie, K., Offertaler, L., Wang, L., and Kunos, G. (2005) J Clin Invest 115, 1298-1305.

Pertwee R G. Pharmacology of cannabinoid receptor ligands. Curr Med Chem. 1999 August; 6(8):635-64.

Pi-Sunyer F X, Aronne L J, Heshmati H M, Devin J, Rosenstock J; for the RIO-North America Study Group. Effect of rimonabant, a cannabinoid-1 receptor blocker, on weight and cardiometabolic risk factors in overweight or obese patients: RIO-North America: a randomized controlled trial. JAMA. 2006; 295:761-775.

Reid A E. Nonalcoholic steatohepatitis. Gastroenterology. 2001 September; 121(3):710-23.

Rinaldi-Carmona M, Calandra B, Shire D, Bouaboula M, Oustric D, Barth F, Casellas P, Ferrara P, Le Fur G. Characterization of two cloned human CB1 cannabinoid receptor isoforms. J Pharmacol Exp Ther. 1996 August; 278(2):871-8.

Rinaldi-Carmona et al., J. Pharmacol. Expt. Ther., 1998, 284:644-650.

Rinaldi-Carmona M., The development of cannabinoid antagonists. Curr Med Chem. 1999 August; 6(8):745-55.

Sambrook et al., "Molecular Cloning: A Laboratory Manual," Second Edition, Cold Spring Harbor Laboratory Press, 1989.

Tuerk C. and Gold L. (1990) Systematic evolution of ligands by exponential enrichment: RNA ligands to bacteriophage T4 DNA polymerase. Science. 3; 249(4968):505-10.

Tuschl T, Zamore P D, Lehmann R, Bartel D P, Sharp P A. Targeted mRNA degradation by double-stranded RNA in vitro. Genes Dev. 1999 Dec. 15; 13(24):3191-7.

Van Gaal L F, Rissanen A M, Scheen A J, Ziegler O, ROssner S; for the RIO-Europe Study Group. Effects of the cannabinoid-1 receptor blocker rimonabant on weight reduction and cardiovascular risk factors in overweight patients: 1-year experience from the RIO-Europe study. Lancet. 2005; 365:1389-1397.

Wells J A, Vasser M, Powers D B. Cassette mutagenesis: an efficient method for generation of multiple mutations at defined sites. Gene. 1985; 34(2-3):315-23.

Wiley J L, Burston J J, Leggett D C, Alekseeva O O, Razdan R K, Mahadevan A, Martin B R. CB1 cannabinoid receptor-mediated modulation of food intake in mice. Br J Pharmacol. 2005 June; 145(3):293-300.

Williams C M, Kirkham T C. Reversal of delta 9-THC hyperphagia by SR141716 and naloxone but not dexfenfluramine. Pharmacol Biochem Behay. 2002 January-February; 71(1-2):333-40.

Yang S Q, Lin H Z, Lane M D, Clemens M, Diehl A M. Obesity increases sensitivity to endotoxin liver injury: implications for the pathogenesis of steatohepatitis. Proc Natl Acad Sci USA. 1997 Mar. 18; 94(6):2557-62.

Zoller M J, Smith M. Oligonucleotide-directed mutagenesis using M13-derived vectors: an efficient and general procedure for the production of point mutations in any fragment of DNA. Nucleic Acids Res. 1982 Oct. 25; 10(20):6487-500.

What is claimed is:

1. A method for treating and/or preventing insulin resistance comprising administering to a subject in need thereof a selective inhibitor of cannabinoid type 2 (CB2) receptor expression, wherein said inhibitor of CB2 receptor expression is selected from the group consisting of antisense RNA or DNA molecules, small inhibitory RNAs (SiRNAs) and ribozymes.

2. The method according to claim 1, wherein said insulin resistance is induced by overeating, high fat diet and/or hyperglycaemic diet.

3. The method according to claim 1, wherein said antisense RNA or DNA molecules, small inhibitory RNAs (SiRNAs) or ribozymes are delivered in association with a vector.

4. The method according to claim 3, wherein said vector is selected from plasmids, phagemids or viral vectors.

* * * * *